US 11,666,740 B2

(12) United States Patent
Trautman et al.

(10) Patent No.: US 11,666,740 B2
(45) Date of Patent: Jun. 6, 2023

(54) APPLICATORS FOR MICRONEEDLES

(71) Applicant: Corium Pharma Solutions, Inc., Boston, MA (US)

(72) Inventors: Joseph C. Trautman, Sunnyvale, CA (US); Douglas Joseph Scott Bourne, Campbell, CA (US); Anthony Le, San Jose, CA (US); Robert Wade Worsham, Sutter Creek, CA (US); Parminder Singh, Union City, CA (US)

(73) Assignee: Corium Pharma Solutions, Inc., Grand Rapids, MI (US)

( * ) Notice: Subject to any disclaimer, the term of this patent is extended or adjusted under 35 U.S.C. 154(b) by 288 days.

(21) Appl. No.: 17/185,746

(22) Filed: Feb. 25, 2021

(65) Prior Publication Data

US 2021/0187263 A1 Jun. 24, 2021

Related U.S. Application Data

(63) Continuation of application No. 15/633,583, filed on Jun. 26, 2017, now Pat. No. 10,946,180, which is a
(Continued)

(51) Int. Cl.
*A61M 37/00* (2006.01)
*A61B 17/20* (2006.01)

(52) U.S. Cl.
CPC ....... *A61M 37/0015* (2013.01); *A61B 17/205* (2013.01); *A61M 2037/0023* (2013.01)

(58) Field of Classification Search
CPC .................. A61M 2037/0023; A61M 37/0015
See application file for complete search history.

(56) References Cited

U.S. PATENT DOCUMENTS 6,322,808 B1 11/2001 Trautman et al.
6,537,242 B1 3/2003 Palmer
(Continued)

FOREIGN PATENT DOCUMENTS

WO WO 2005/065765 A1 7/2005
WO WO 2006/055771 A1 5/2006
(Continued)

OTHER PUBLICATIONS

"Extend", Merriam-Webster Online Dictionary, <http://www.merriam-webster.com/dictionary/extend>.
(Continued)

*Primary Examiner* — Deanna K Hall
(74) *Attorney, Agent, or Firm* — Goodwin Procter LLP

(57) ABSTRACT

An applicator for a microprojection array is described. In one embodiment, the applicator comprises an energy-storing element. Application of force causes the compressed energy-storing element to extend or transition from first and second configurations, releasing stored energy to deploy a holding member in the application which is configured to hold an array of microprojections. In another embodiment, the applicator comprises an energy storing element with two stable configurations, a first stable configuration and second stable configuration. Application of force causes the energy-storing element to transition from the higher energy first stable configuration to the lower energy second stable configuration, releasing the difference in energies of the two states to deploy a holding member in the application which is configured to hold an array of microprojections.

23 Claims, 18 Drawing Sheets

Specification includes a Sequence Listing.

Related U.S. Application Data continuation of application No. 13/100,924, filed on May 4, 2011, now Pat. No. 9,687,640.

(60) Provisional application No. 61/331,175, filed on May 4, 2010.

(56) References Cited

U.S. PATENT DOCUMENTS

| | | |
|---|---|---|
| 6,743,211 B1 | 6/2004 | Prausnitz et al. |
| 6,855,131 B2 | 2/2005 | Trautman et al. |
| 7,097,631 B2 | 8/2006 | Trautman et al. |
| 7,131,960 B2 | 11/2006 | Trautman et al. |
| 9,687,640 B2 | 6/2017 | Trautman et al. |
| 2002/0032415 A1 | 3/2002 | Trautman et al. |
| 2002/0087182 A1 | 7/2002 | Trautman et al. |
| 2002/0091357 A1 | 7/2002 | Trautman et al. |
| 2003/0220610 A1 | 11/2003 | Lastovich et al. |
| 2005/0096586 A1 | 5/2005 | Trautman et al. |
| 2006/0095061 A1 | 5/2006 | Trautman et al. |
| 2006/0253079 A1 | 11/2006 | McDonough et al. |
| 2007/0027427 A1 | 2/2007 | Trautman et al. |
| 2008/0009825 A1 | 1/2008 | Ringsred et al. |
| 2008/0114298 A1 | 5/2008 | Cantor et al. |
| 2008/0183144 A1 | 7/2008 | Trautman et al. |
| 2008/0195035 A1 | 8/2008 | Frederickson et al. |
| 2008/0269685 A1 | 10/2008 | Singh et al. |
| 2009/0155330 A1 | 7/2009 | Ghartey-Tagoe et al. |
| 2017/0361079 A1 | 12/2017 | Trautman et al. |

FOREIGN PATENT DOCUMENTS

| | | |
|---|---|---|
| WO | WO 2006/055795 A | 5/2006 |
| WO | WO 2007/002521 A2 | 1/2007 |
| WO | WO 2007/002522 A1 | 1/2007 |
| WO | WO 2007/002523 A | 1/2007 |
| WO | WO 2007/081430 A2 | 1/2007 |
| WO | WO 2007/028167 A2 | 3/2007 |
| WO | WO 2007/124411 A | 11/2007 |

OTHER PUBLICATIONS

"Extend", Macmillan Online Dictionary, <http://www.macmillandictionary.com/dictionary/american/extend>.

"Heparin pregnancy and breast feeding warnings", Drugs.com, accessed Oct. 8, 2009, <http://www.drugs.com/pregnancy/heparin.html>.

International Search Report from related PCT Patent Application No. PCT/US2011/035221 dated Jan. 10, 2012, application now published as WO 2011/140240 on Nov. 10, 2011.

Rydberg et al., "Low-molecular-weight heparin in preventing and treating DVT", Am. Fam. Physician, vol. 59, No. 6, pp. 1607-1612 (1999).

SEQUENCE LISTING

```
<160> NUMBER OF SEQ ID NOS: 1

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```

APPLICATORS FOR MICRONEEDLES

CROSS-REFERENCE TO RELATED APPLICATIONS

This application is a continuation of U.S. application Ser. No. 15/633,583, filed Jun. 26, 2017, which is a continuation of U.S. application Ser. No. 13/100,924, filed May 4, 2011, now U.S. Pat. No. 9,687,640, which claims the benefit of U.S. Provisional Application No. 61/331,175, filed May 4, 2010, each of which is incorporated by reference herein.

REFERENCE TO SEQUENCE LISTING

A Sequence Listing is being submitted electronically via EFS in the form of a text file, created Feb. 24, 2021, and named 0915000920SequenceListing.txt (842 bytes), the contents of which are incorporated herein by reference in their entirety.

TECHNICAL FIELD

The subject matter described herein relates generally to drug delivery using microneedles or other microprojections, and more specifically to applicators for applying an array of microprojections to the stratum corneum.

BACKGROUND

Arrays of microneedles were proposed as a way of administering drugs through the skin in the 1970s, for example in expired U.S. Pat. No. 3,964,482. Microneedle arrays can facilitate the passage of drugs through human skin and other biological membranes in circumstances where ordinary transdermal administration is inadequate. Microneedle arrays can also be used to sample fluids found in the vicinity of a biological membrane such as interstitial fluid, which is then tested for the presence of biomarkers.

In recent years it has become more feasible to manufacture microneedle arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use.

In addition to cost, integrity and sterility, a further issue with microneedle arrays is bioavailability of the active agent. An intravenous injection delivers a precise quantity of an active agent to the circulation. A subcutaneous or intramuscular injection delivers a precise quantity of an active agent into the tissue, but the quantity of active agent delivered to the circulation and the rate at which active ingredient is delivered are affected by the type of surrounding tissue, circulation, and possibly other factors. When a drug is delivered orally, the resulting blood levels may exhibit substantial variation among patients due to metabolism and other factors, but minimal therapeutic levels can be assured for most patients, for example, because the rate of metabolism has an upper limit and because there is long experience with the absorption of many drugs from oral formulations. When a drug is delivered to unmodified skin by a conventional transdermal patch, the bypassing of the hepatic circulation may lessen the effect of liver metabolism on bioavailability. On the other hand, with a conventional transdermal patch, differences in skin permeability are an additional factor leading to differences in bioavailability.

Microneedles manipulate the permeability of the skin with respect to the active agent. Variability in the permeability enhancement created by different applications of the microneedles will result in variations in the rate of transfer through the skin, the amount transferred through the skin and the bioavailability. Variability of skin permeability enhancement on the application of a microneedle array can result from application on different patients. Particular concern exists, of course, if the enhancement is small in particular patient populations so that the administration of the drug will not produce a therapeutically effective dosing (e.g., adequate blood levels) in those populations. Concern may arise also if the enhancement is sometimes undesirably small in a patient, even if at other times the enhancement is as expected in that patient, depending on details of how and where the microneedle array is applied.

A typical microneedle array comprises microneedles projecting from a base of a particular thickness, which may be of any shape, for example square, rectangular, triangular, or circular. The microneedles themselves may have a variety of shapes. While an array could be pressed by hand into skin, it has also been proposed to use a variety of devices to hold the microneedle array as it is being applied or to facilitate in one way or another the process of microneedle array application to the skin or other biological membrane. Such devices may broadly be referred to as "applicators." Applicators may for example reduce the variations in force, velocity, and skin tension that occur when a microneedle array is pressed by hand into the skin. Variations in force, velocity and skin tension can result in variations in permeability enhancement.

In some applications of microneedle arrays, they may be applied to the skin or other biological membrane in order to form microchannels and then are more or less immediately withdrawn. In other applications the microneedle array may be held in place for a longer period of time. The design of the applicator may naturally be influenced by how long the microneedles are expected to stay in place.

Applicators for microneedles comprising components which have two stable states have been described in U.S. Published Patent Application No. 2008/0183144. The existence of two stable states is a feature generally desired in an applicator because the energy difference between the two stable states can allow each use of the applicator to employ a fixed amount of energy in order to cause penetration, improving reproducibility. However, a limitation of this earlier approach is that the energy delivered to the microstructure array is both limited and variable. The earlier approach was dependent on the input of the user for both energy and velocity, and variation in application technique had a significant effect on the ability of the device to enhance the permeability of the skin.

In some other prior art applicator designs, the energy storage element, such as a spring or elastic element, may exert forces on one or more components of the applicators, leading to dimensional distortion and creep over an extended period of time. These effects are undesirable as they lead to variations in the applicator geometry and a loss in the stored elastic energy over time. Therefore, there is a need for an applicator which has energy storage elements that do not exert forces on one or more components of the applicator.

In the use of microneedle arrays, particularly when the arrays are kept in place for a prolonged period of time, devices to transport the drug substance to the skin may be employed. A very simple such device may, for example, comprise a reservoir for liquid or solid drug substance which is kept in contact with the base, with the liquid drug substance flowing through small apertures in the base or by diffusion when solid drug substance is used. Another device suitable for delivering the drug substance to skin is described in U.S. Published Patent Application No. 2005/0094526. Rotary applicators have been disclosed in U.S. Published Patent Application No. 2004/0087992. There is some disclosure relating to applicators, for example, in U.S. Pat. Nos. 6,537,242, 6,743,211 and 7,087,035.

There is a need in the art for applicators and related devices suitable for use with microneedle arrays, for example, in order to assist in making the process of drug delivery more user friendly and uniform across patients and for different applications to the same patient.

BRIEF SUMMARY

In one aspect, an applicator for a microprojection array is provided. The applicator comprises an energy-storing element which has a first stable configuration and second stable configuration, wherein application of force can cause the energy-storing element to transition from the first stable configuration to the second stable configuration, and wherein the force necessary for the energy storing element to transition from the first stable configuration to the second stable configuration is lower than the force necessary for the element to transition from the second stable configuration to the first stable configuration. The applicator also comprises an actuating member that can convey external force to the energy-storing element, a microprojection-holding member connected to the actuating member and which is acted on by the energy-storing element when it transitions from the first stable configuration to the second stable configuration, an outer cover with an opening into which the actuating member fits slidably, and a skin-contacting member comprising a portion which can lie flat against skin, wherein the skin-contacting member fits the outer cover and contacts the energy-storing element when it is in its first configuration.

In one embodiment, the energy-storing element has an axis of symmetry and n-fold rotational symmetry for some integer n. In another embodiment, application of force to the energy-storing element in a direction of its axis of symmetry causes it to transition from the first stable configuration to the second stable configuration.

In another embodiment, an applicator for a microprojection array comprises a housing having a surface with an elongated opening having platforms on opposite sides of the opening. An actuation member comprising a surface upon which a microprojection array can be attached, a generally washer-shaped surface on which an energy-storage member can be placed, and a surface capable of mating with the platforms on the opening of the housing and capable of fitting through the opening is included. An energy-storage member is situated between the actuation member and the housing, and a skin-contacting area which is generally washer-shaped is connected to the housing. In one embodiment, when the actuation member is mated with the platforms on the opening, the energy-storage member is compressed, and when the actuation member is moved within the opening so that it no longer mates with the platforms, the energy-storage member is free to expand and in so doing moves the actuation member.

In one embodiment, the energy-storage member is in the form of a wave spring. In other embodiments, the energy storage member has an n-fold rotational axis of symmetry of between about 3-22, more preferably 3-18 or 3-9, and still more preferably between 3-6.

In another embodiment, the actuator member moves within the outer cover between a first position and a second position, wherein in its first position the actuator member extends outwardly from and beyond an upper surface of the outer cover.

In another embodiment, the actuator member moves within the outer cover between a first position and a second position, wherein in its first position the actuator member is recessed within the outer cover.

In yet another embodiment, the microprojection array is attached to the microprojection-holding member, the microprojection array comprises a base, and the level of the microprojection array's base is below a skin-contacting surface of the skin-contacting member following actuation of the actuating member.

In still another embodiment, the level of the microprojection array's base below the skin-contacting surface of the skin-contacting member is between about 0.001 inches to about 0.200 inches, more preferably between about 0.001 inches to about 0.125 inches, still more preferably from about 0.030 inches to about 0.090 inches.

In another embodiment, the energy-storing element is in mechanical coupling relationship with the microprojection-holding member when the energy-storing element is in its first stable configuration.

In another aspect, an applicator for a microprojection array is provided. The applicator comprises (a) a housing having a surface with an elongated opening having platforms on opposite sides of the opening; (b) an actuation member comprising a surface upon which a microprojection array can be attached, a generally washer-shaped surface on which an energy-storage member can be placed, and a surface capable of mating with the platforms on the opening of the housing and capable of fitting through the opening; (c) an energy-storage member situated between the actuation member and the housing; and (d) a skin-contacting area which is generally washer-shaped connected to the housing. When the actuation member is mated with the platforms on the opening, the energy-storage member has a first force of stored energy, and when the actuation member is moved within the opening so that it no longer mates with the platforms, the energy-storage member releases its stored energy and in so doing moves the actuation member.

In one embodiment, the energy-storage member when mated with the platforms on the opening has a first force of stored energy by virtue of its being compressed.

In yet another aspect, an applicator is provided. The applicator comprises (a) a housing having a first member with a central opening and a second member having a skin contacting surface; (b) an actuation member disposed in the central opening and comprising a surface upon which a microprojection array can be attached and a groove extending circumferentially; and (c) an energy-storage member having an inner edge and an outer edge, and situated within the housing initially in a first stable configuration such that the inner edge is disposed in the groove and its outer edge is in contact with the second member. Application of force to the actuation member moves the energy-storage member from its first stable configuration to a second stable configuration wherein the outer edge is no longer in contact with the second member.

In one embodiment, the outer edge of the energy storage member in its second stable configuration is in contact with the first member.

In another embodiment, a microprojection array holder engages the actuation member, the engagement of the actuation member and the microprojection array holder defining the groove.

In still another embodiment, the energy-storage member has an axis of symmetry and n-fold rotational symmetry for some integer n, wherein application of force in a direction of the axis of symmetry causes the energy-storing element to transition from the first stable configuration to the second stable configuration, and wherein the force necessary for the energy storing element to transition from the first stable configuration to the second stable configuration is lower than the force necessary for the element to transition from the second stable configuration to the first stable configuration.

In yet another embodiment, the energy-storing element is of generally frustoconical shape with slots from the top of the frustum, from the bottom of the frustum, or from both.

In another aspect, any of the applicator embodiments described herein further comprises a safety mechanism to prevent movement of the actuation member in a direction that deploys the microprojection array.

In one embodiment, the safety mechanism comprises a protective cap over the applicator housing. In another embodiment, the safety mechanism comprises a pin movably inserted into the actuation member on an applicator.

In another aspect, a device comprising an applicator in accord with any of the aspects and embodiments described herein and a microprojection array comprising an active agent is provided.

In another aspect, a method for applying a microprojection array to a biological barrier is provided. The method comprises providing an applicator as described herein, the applicator including or capable of including a microprojection array. The applicator is contacted with the biological barrier, and an actuating member on the applicator is activated, to initiate movement of the energy-storage member from its first stable configuration to its second stable configuration. Movement of the energy-storage member induces movement of the microprojection array, directly or indirectly, causing it to forcibly contact the biological barrier. In embodiments where the microprojection array comprises a therapeutic or prophylactic agent, the method achieves administration of the agent to a subject.

Additional embodiments of the present method, microprojection array, kit, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIGS. 11A-11B are perspective views of an applicator according to yet another embodiment, wherein FIG. 11A depicts the applicator in a configuration prior to deployment or actuation by a user, and FIG. 11B depicts the same applicator after deployment or actuation by a user.

FIGS. 12A-12B are cross-sectional side views of a first embodiment of internal components of an applicator according to the applicator of FIGS. 11A-11B, wherein FIG. 12A depicts the applicator in a configuration prior to deployment or actuation by a user, and FIG. 12B depicts the same applicator after deployment or actuation by a user.

FIGS. 13A-13B are cross-sectional side views of a second embodiment of internal components of an applicator according to the applicator of FIGS. 11A-11B, wherein FIG. 13A depicts the applicator in a configuration prior to deployment or actuation by a user, and FIG. 13B depicts the same applicator after deployment or actuation by a user.

DETAILED DESCRIPTION

Figure 1A:
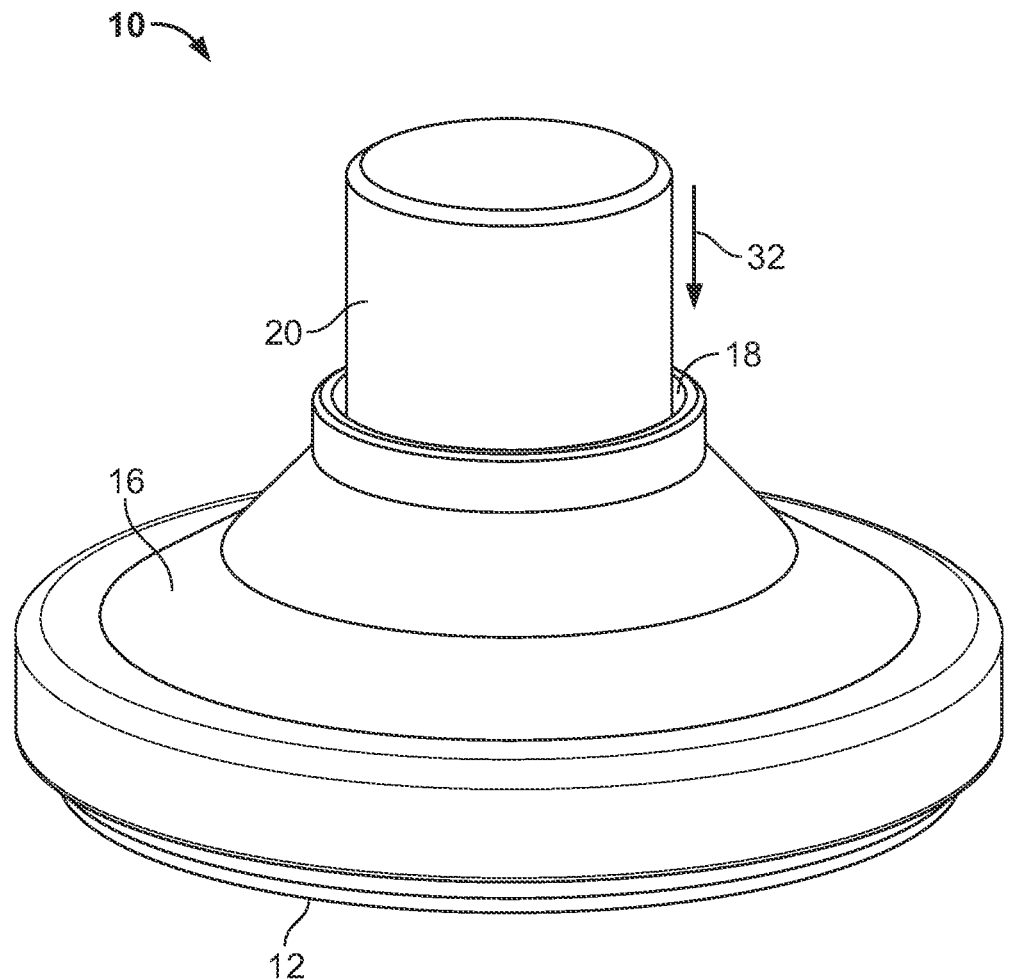
FIGS. 1A-1B are views of an applicator as described herein, the applicator shown in perspective views (FIG. 1A), a sectional view (FIG. 1B) and an exploded view (FIG. 1C).

Before describing the present subject matter in detail, it is to be understood that this invention is not limited to specific materials or device structures, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "an active ingredient"

includes a plurality of active ingredients as well as a single active ingredient, reference to "a temperature" includes a plurality of temperatures as well as single temperature, and the like.

For information regarding words which have multiple meanings, reference is made to *The Oxford English Dictionary* (2d ed. 1989) and the *McGraw-Hill Dictionary of Scientific and Technical Terms* (6th ed. 2002), which are incorporated by reference herein. The inclusion of these references is not intended to imply that every definition in them is necessarily applicable here, as persons of skill in the art would often see that a particular definition is not in fact applicable in the present context.

In this application reference is often made for convenience to "skin" as the biological membrane which the microneedles penetrate. It will be understood by persons of skill in the art that in most or all instances the same inventive principles apply to the use of microneedles to penetrate other biological membranes such as, for example, those which line the interior of the mouth or biological membranes which are exposed during surgery.

In this application reference is also made to "microneedles" as the type of microprotrusion or microprojection which is being employed. It will be understood by persons of skill in the art that in many cases the same inventive principles apply to the use of other microprotrusions or microprojections to penetrate skin or other biological membranes. Other microprotrusions or microprojections may include, for example, microblades as described in U.S. Pat. No. 6,219,574 and Canadian patent application no. 2,226,718, and edged microneedles as described in U.S. Pat. No. 6,652,478.

In discussing the applicators of this invention, the term "downward" is sometimes used to describe the direction in which microprotrusions are pressed into skin, and "upward" to describe the opposite direction. However, those of skill in the art will understand that the applicators can be used where the microprotrusions are pressed into skin at an angle to the direction of the earth's gravity, or even in a direction contrary to that of the earth's gravity. In many applicators of the invention, the energy for pressing the microprotrusions is provided primarily by an energy-storage member and so efficiency is not much affected by the orientation of the skin relative to the earth's gravity.

The sizes of the microneedles and other microprotrusions for use with the applicators described herein will be a function of the manufacturing technology and of the precise intended application (e.g., the active agent to be delivered, whether it is contained in the microprojections, etc.). In general, however, microneedles and other microprotrusions used in practice may be expected to have a length of about 20 to about 1000 microns, more preferably from about 50 to about 750 microns and most preferably from about 100 to about 500 microns. Often it will be desired that the microprotrusions will be long enough to penetrate through the stratum corneum layer of skin at some suitable point of application on the human body, for example the thigh, hip, arm, or torso.

The term "microneedle array" for purposes herein is intended to denote a two-dimensional or a three-dimensional arrangement of microneedles. The arrangement may be regular according to a repeating geometric pattern or it may be irregular. Similarly, "microprojection array" denotes a two-dimensional or three-dimensional arrangement of microprojections.

In a first aspect, an applicator for microprojection arrays is provided in which the velocity at the time of microprojection array contact with skin is controlled within a predetermined range. The applicator operates when an actuating element is pressed with a force which is above a threshold. The velocity of contact is substantially independent of the precise force employed to press the actuating element. The applicator comprises an energy-storing element.

In a further aspect, a method for inserting microprojections in an array of microprojections into skin or another biological barrier is provided. The method comprises placing an applicator in contact with the barrier into which the array is to be inserted and operating an actuating element which forms part of the applicator with a force which lies above a predetermined threshold. The velocity of the microprojection array and the energy per microstructure at the time of contact with skin need to be above a threshold and may be controlled within a predetermined range.

Applicators contemplated herein will commonly have two states or configurations. In the first state or configuration, the applicator has the microprojection array recessed. This is expected to be the state of the applicator following manufacturing and during shipping and storage. In the second state or configuration, which is arrived at by pressing or otherwise operating the actuating element, the microprojection array projects modestly outward from the applicator.

The velocity of the microprojection array at the time of contact with skin may be adjusted, for example, by varying the amount of stored energy in the energy-storing element. This is done, for example, by controlling the energy-storing element's geometric design and the properties of the material(s) out of which the energy-storing element is made. The energy-storing element may have a compressed form in which the degree of compression (e.g., in one spatial direction) controls the amount of energy stored.

When the energy storing element is stored in compressed form, a variety of mechanisms external to the element, but forming part of the applicator, may be employed to release the compression and allow the element to uncompress and therefore release some or all of its energy.

Alternatively, the energy-storing element may be bistable in that it has two stable states in which energy is stored. The two states may have different energies. The amount of stored energy may be, for example, in the range of about 0.1 J to about 10 J, or in the range of about 0.25 J to about 1 J. The energy storage element having two bi-stable states is highly advantageous because in its higher energy state, the energy storage element does not exert any significant forces on the applicator components, thereby alleviating the problems with dimensional distortion and creep over time. Reducing the dimensional distortion and creep lead to maintaining the same stored elastic energy for an extended period of time. Maintaining the same stored elastic energy over a period of time is important for having an extended shelf life of at least preferably 6 months, more preferably 12 months, and most preferably 24 months.

The velocity of the microprojection array at the time of contact with the skin may lie, for example, within the range of 0.1 m/s to 20 m/s, or within the range of 0.5 m/s to 10 m/s. In general, the stored energy may be employed in moving the microprojection array into contact with the skin as well as in overcoming any forces (e.g., from other components of the applicator) acting on the microprojection array. In addition, the stored energy may be employed in moving other components which, in accordance with the design of the applicator, must also move as the microprojection array moves towards the skin.

The velocity of the microprojection array is preferably reproducible. For example, the standard deviation of the velocity in a number of applications carried out with different applicators of the same design or by different persons using the same applicator may be less than about 10% of the average velocity, less than about 5%, or less than about 1%.

It may be desired that the applicator comprise one or more components which have rotational symmetry about an axis perpendicular to the microprojection array. For example, the applicator may comprise components which have n-fold rotational symmetry (symmetry under rotations of 360/n degrees), for some integer n>1, for example n=2, 3, 4, 5, or 6. To give an example, the clip depicted in FIG. 3B, a component of an applicator described herein, has 3-fold rotational symmetry.

It may be desirable that the energy-storing element be in mechanical coupling relationship with the microprojection array or a member holding the array at all times. An alternative design, however, would allow the energy-storing element not to be coupled to the microprojection array during the stored state of the applicator but only to come into contact with the array or a member holding the array during the process of actuation. Such contact may occur at a nonzero velocity, although it is desirable that this nonzero velocity be low, for example below about 0.1 cm/s, or below about 0.25 cm/s or below about 1 cm/s.

Following contact of the microneedle array with skin or another barrier, there may be a modest bounce of the array against the skin given that skin has elastic properties. The microneedle array may then settle, pressed by the applicator, into the skin at a level which is modestly below the original level of the skin. The force with which the microprojection array is pressed into the skin may be, for example, between about 0.1 and about 10 N/cm$^2$. The level of the microprojection array's base below the skin is about 0.001 inches (0.00254 cm) or greater, and in other embodiments is between about 1/16 inch (0.0625 inches or 0.159 cm) and about 3/16 inch (0.188 inches or 0.476 cm), or between about 1/16 inch (0.0625 inches or 0.159 cm) to about 1/8 inch (0.125 inches or 0.318 cm).

In a common arrangement where a compressed energy-storage device is employed, the applicator has a primary member, which is contacted with skin when the applicator is to be used. The microprojection array is attached to a retaining member which holds the energy storage device in compression. The retaining member is held in place by a flexible mechanism. The actuation mechanism causes the flexible mechanism to be displaced or elastically deformed in such a way that the retaining member ceases to be restrained. The energy-storage device is then free to expand or to move between first and second configurations, moving the retaining member, and the microprojection array is then displaced towards the skin.

Figure 1B:
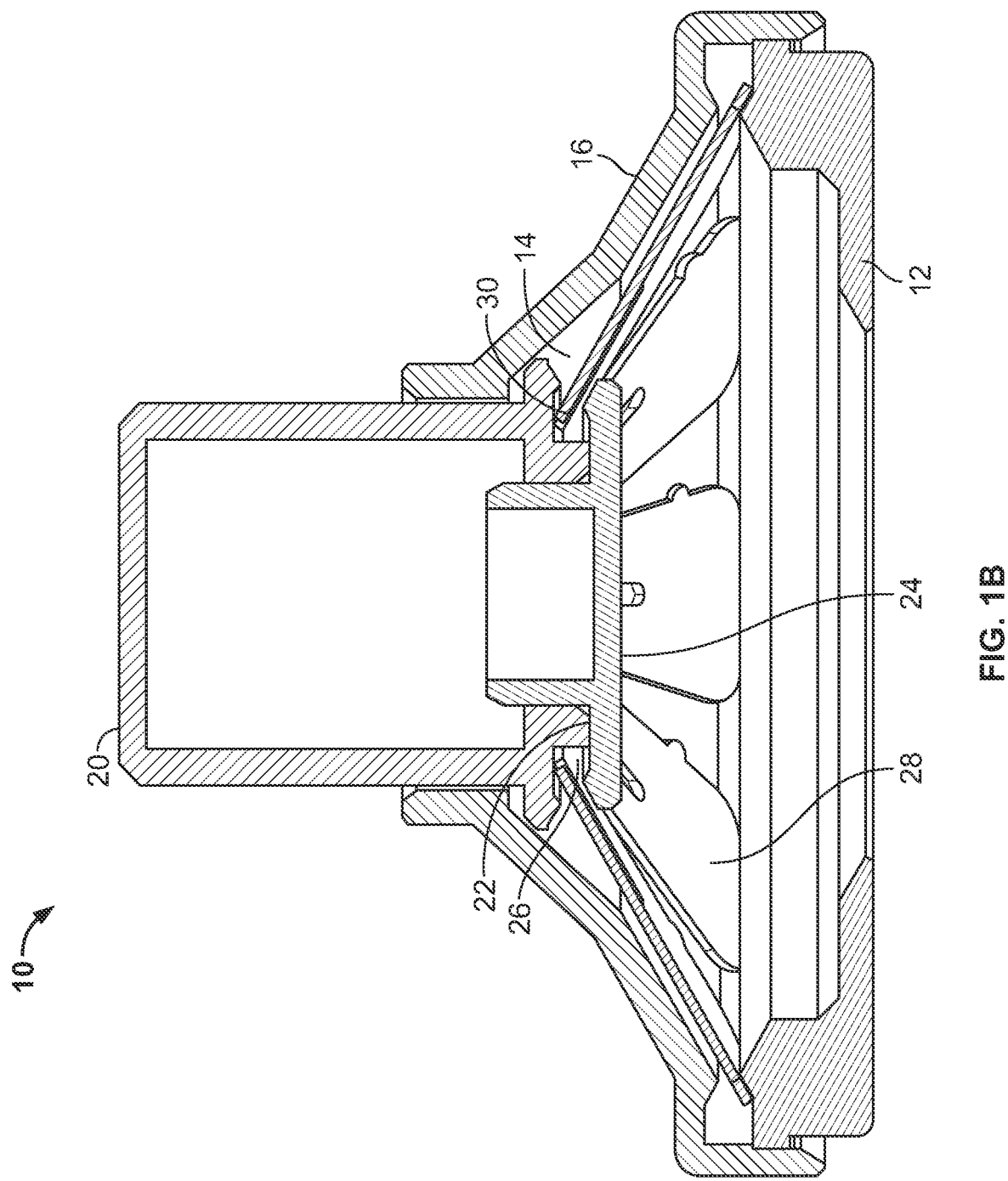
Figure 1C:
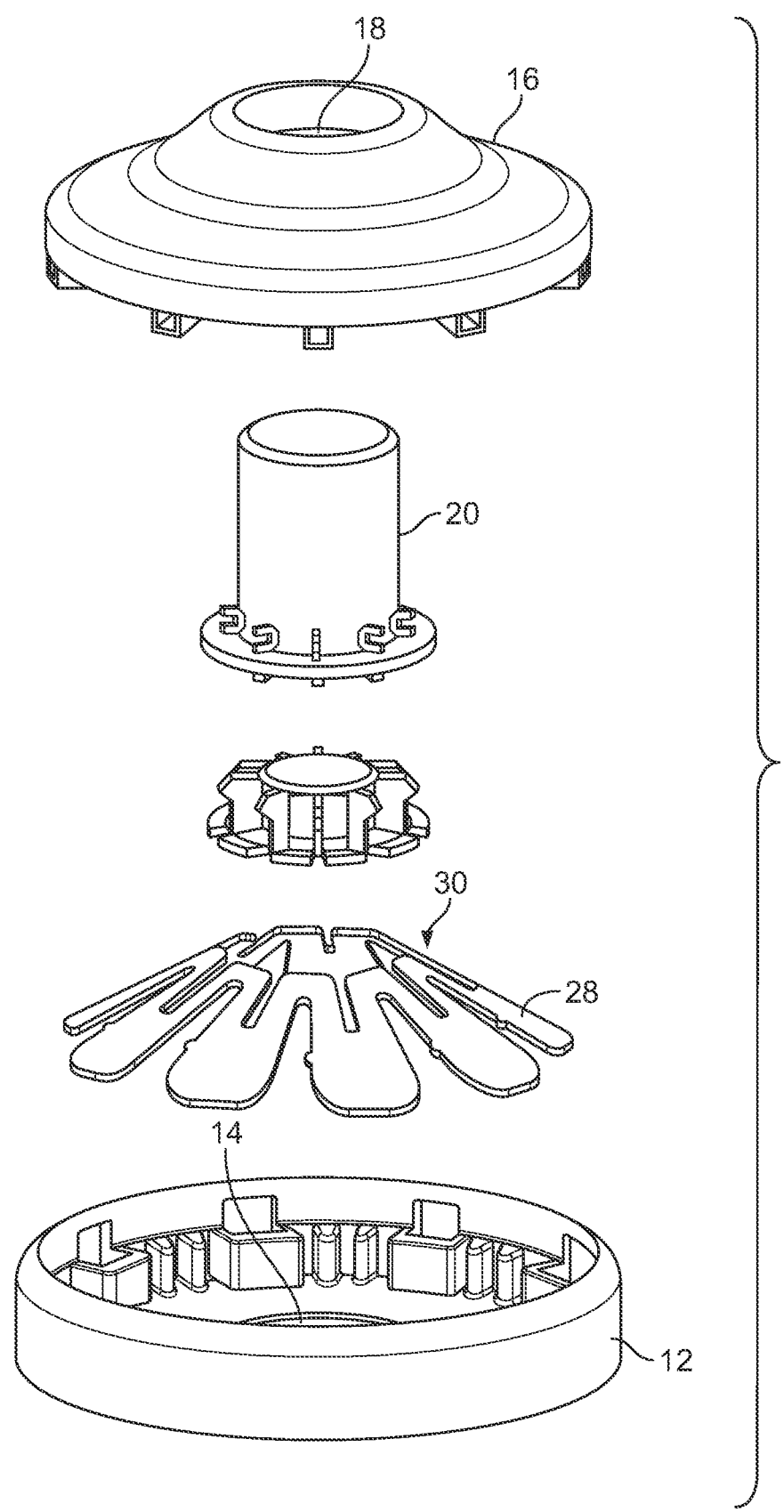
FIGS. 1D-1E show the applicator of FIGS. 1A-1C in perspective view (FIG. 1D) and in a cross-sectional view (FIG. 1E) after actuation of its actuating member.
FIGS. 1F-1T are perspective views of embodiments of energy-storage elements for use in an applicator as described herein.
FIGS. 1U-1V illustrate movement of an energy-storage element between its first stable configuration and its second stable configuration.

Turning now to the drawings, FIGS. 1A-1C depict several views one possible arrangement of an applicator 10. The applicator comprises a skin contacting element 12 which has an opening 14 in its center, and, in this embodiment, has complete rotational symmetry. Skin-contacting element 12 mates with an applicator housing 16 which, in this embodiment, also has complete rotational symmetry and is manufactured from a rigid material (e.g., a polymeric, filled polymeric, composite, or metal material) which preferably does not visibly flex during operation of the device). It will be appreciated that the housing can also be semi rigid, semi-flexible, or flexible, if desired. Housing 16 has an opening 18 at the top, through which an actuating member 20 slidingly fits, as seen best in FIG. 1B, connected to a bottom surface 22 of actuating member 20 is a holder 24 which holds a microprojection array (which is not shown in FIGS. 1A-1C). When bottom surface 22 and the upper surface of holder 24 are in contact, a groove 26 is defined which again has complete rotational symmetry. A bistable energy-storage member 28 having an approximately frustoconical form has an inner edge 30 positioned within groove 26. The energy-storage member of this embodiment is referred to herein as a "slotted spring", described in further detail hereinbelow.

Figure 1D:
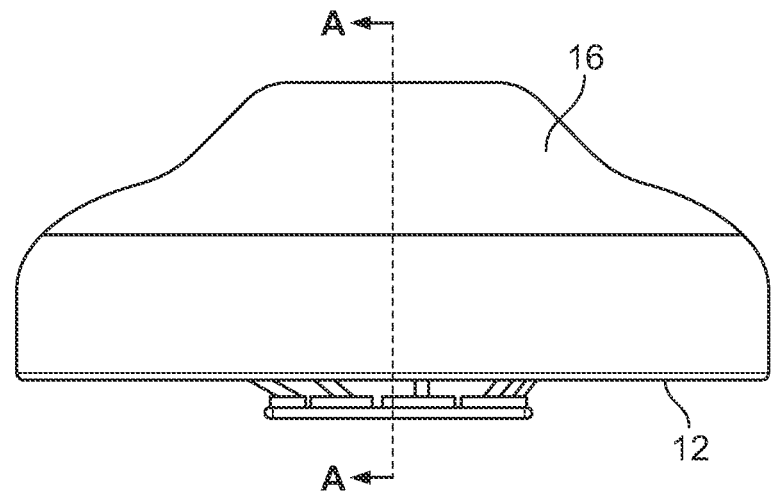
Figure 1E:
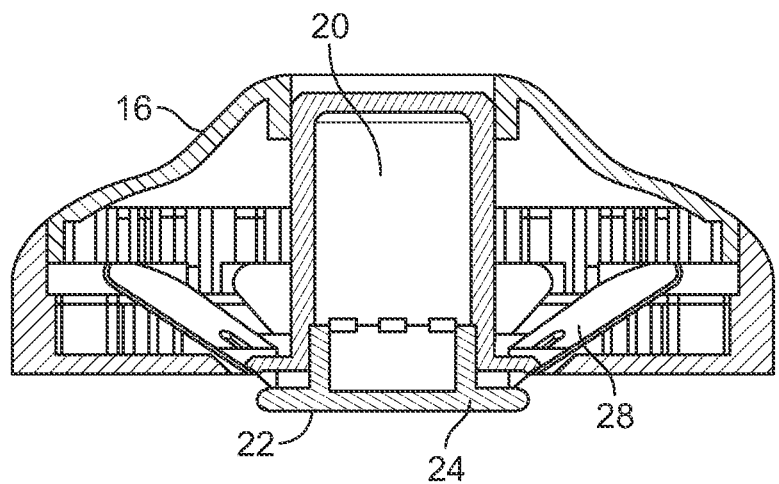

FIGS. 1D-1E illustrate the applicator after actuation of actuating member 20. Housing 16 and its lower portion with skin contacting element 12 are shown in FIG. 1D, where actuating member 20 is not visible because it has been depressed and is fully retained within the housing. Extending slightly beyond the skin contacting element 12 is the bottom surface of the actuating member on which an array of microprojections is held. FIG. 1E is a cross-sectional view taken along line A-A in FIG. 1D, where the actuating member contained within the housing is visible. Also visible is the configuration of the slotted spring member 28 where its inner edge 30 is in a second position relative to it is position prior to actuation, as depicted in FIG. 1B. Specifically, inner edge 30 of the energy-storage member is at a horizontal plane that approaches or approximates the horizontal plane of the edge of the slotted spring prior to use. This transition and inversion of the spring element are described in more detail below.

The materials from which the applicator components are manufactured can be selected from a wide variety known to a skilled artisan. For example, a filled polymer material is suitable for manufacture of the outer cover, the actuating member and/or the microprojection holding member. A skilled artisan will understand the various material properties to be considered when selecting a suitable material for each component part.

Figure 1F:
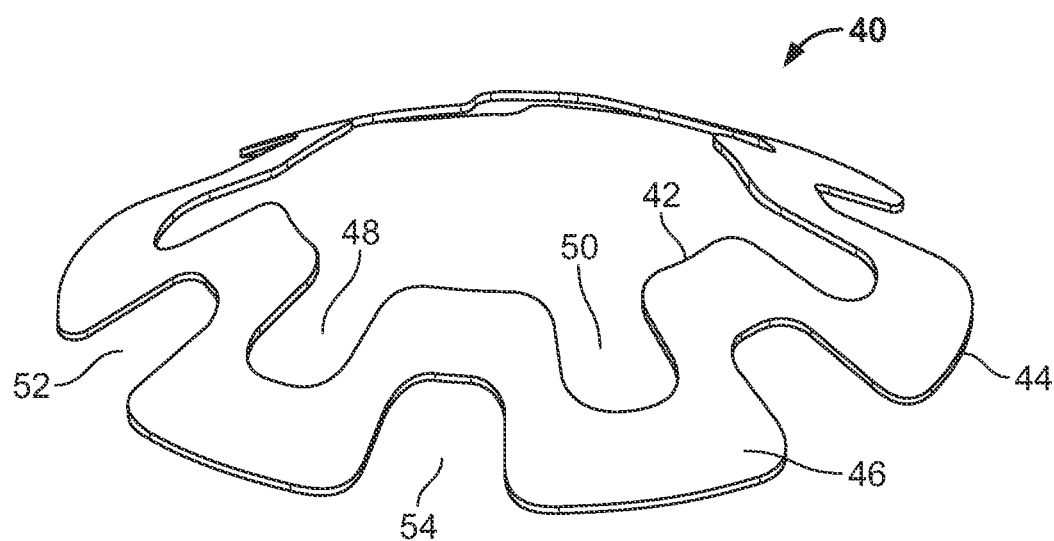
Figure 1G:
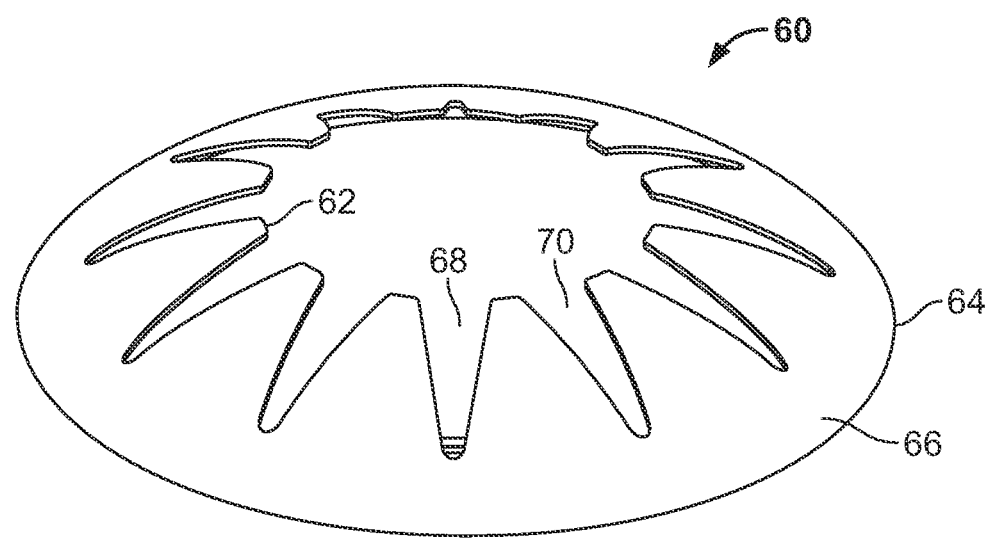
Figure 1H:
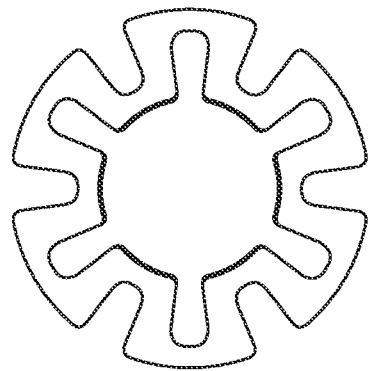
Figure 1I:
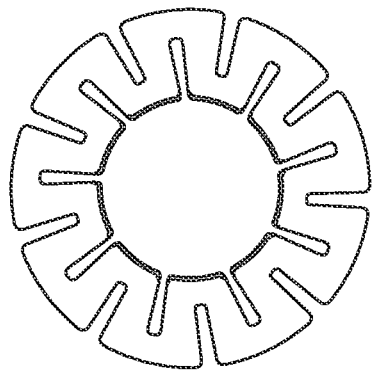
Figure 1J:
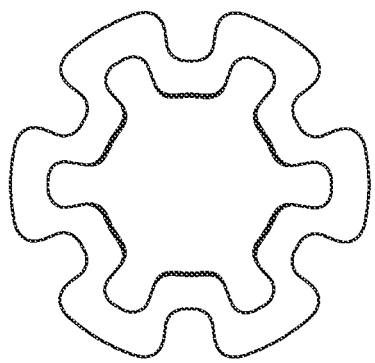

FIGS. 1F-1G are perspective views of two different embodiments of energy-storage members for use in an applicator as described herein, such as that depicted in FIGS. 1A-1E. Energy-storage member 40 of FIG. 1F is substantially in the shape of a washer, and more specifically approximately a frustoconical shape. Inner rim 42 of the member and outer rim 44 of the member define a disc region 46. Upper slots, such as upper slots 48, 50, are cut into the disc region. Lower slots, such as lower slots 52, 54, are cut into the disc region from the outer rim 44. The upper and lower slots are offset from one another, so that a lower slot is positioned between adjacent upper slots, and vice versa. The slots serve to reduce strain of the material during its movement between its first and second stable configurations, as will be described.

FIG. 1G illustrates an alternative embodiment of an energy-storage member 60. Energy-storage member 60 of FIG. 1G is substantially in the shape of a washer, and more specifically a frustoconical shape. Inner rim 62 of the member and outer rim 64 of the member define a disc region 66. A plurality of slots, such as slots 68, 70, are cut into the disc region. The slots serve to reduce strain of the material during its movement between its first and second stable configurations, as will be described.

Figure 1K:
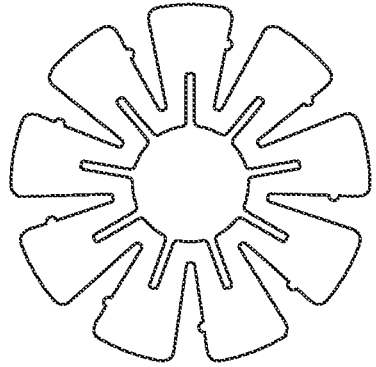
Figure 1L:
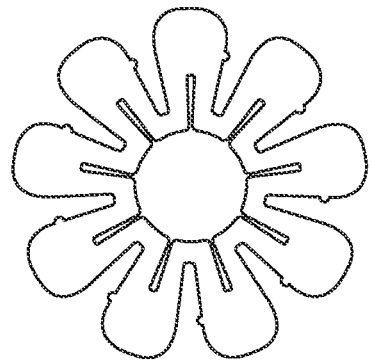
Figure 1M:
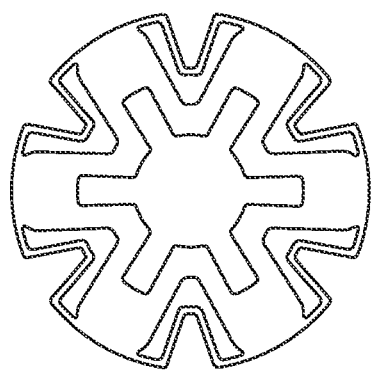
Figure 1N:
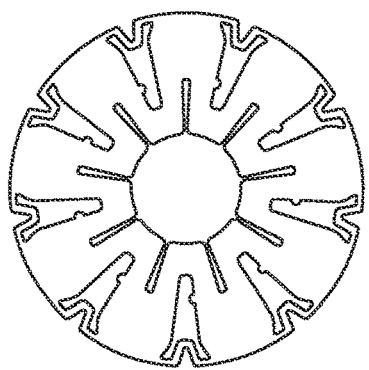
Figure 1O:
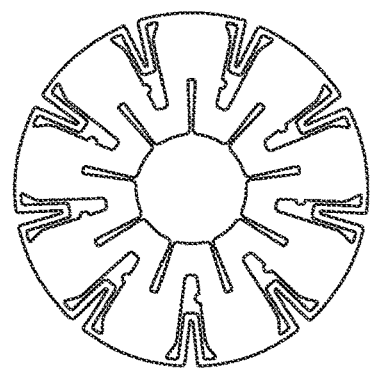
Figure 1P:
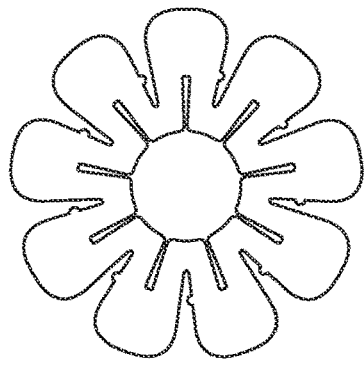
Figure 1Q:
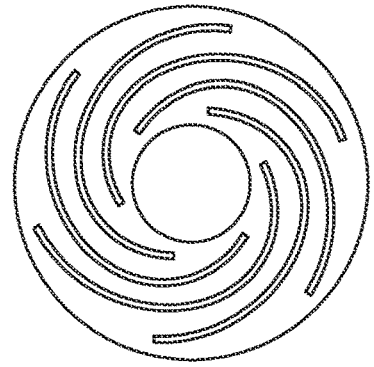
Figure 1R:
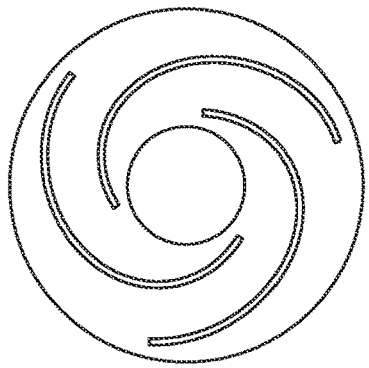
Figure 1S:
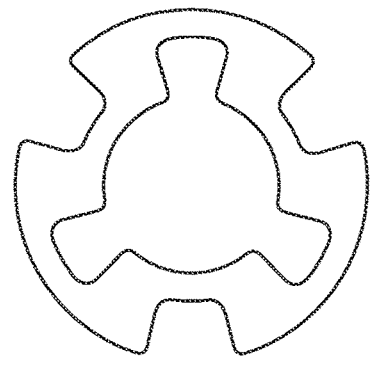
Figure 1T:
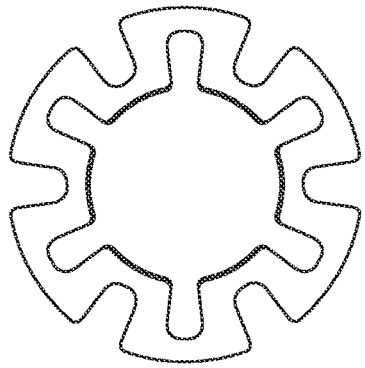
Figure 1U:
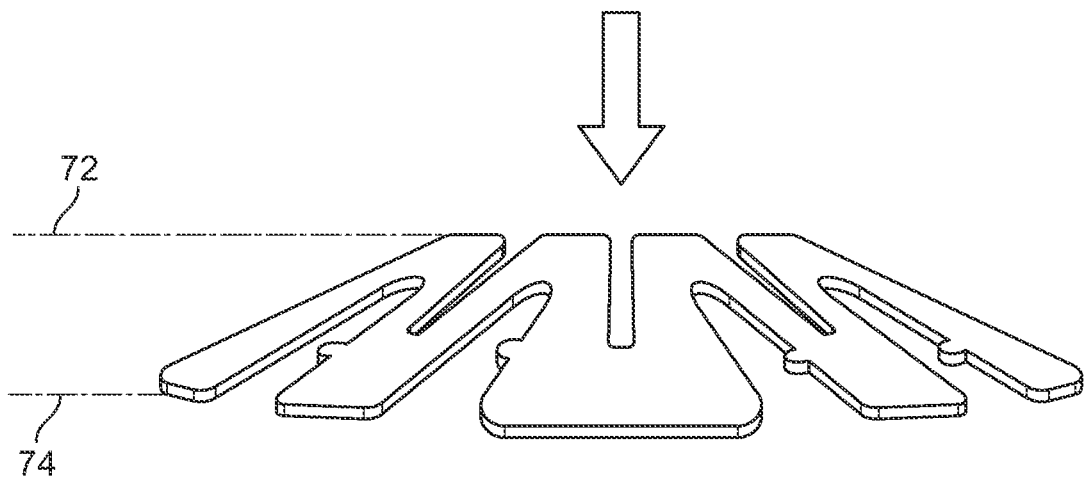
Figure 1V:
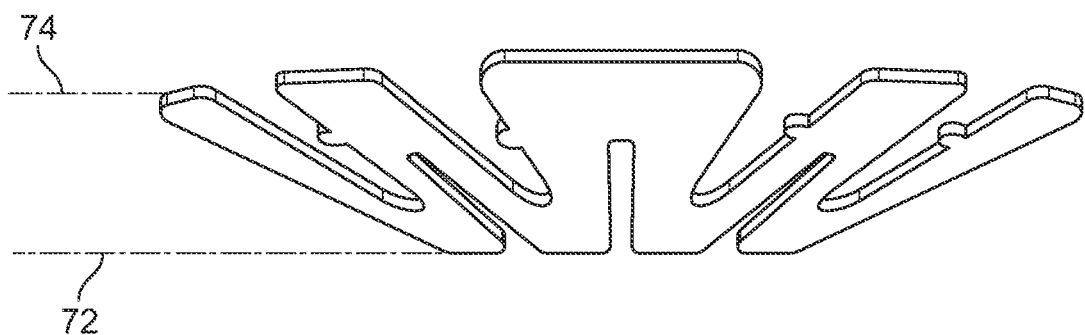

The energy-storage members of the present applicator are movable between first and second stable configurations. In the first stable configuration, the inner edge (or rim) of the energy-storage member lies in a first horizontal plane 72 and the outer edge (or rim) of the energy-storage member lies in a second horizontal plane 74 that is lower than the first horizontal plane, as depicted in FIGS. 1U-1V. Application of force to the energy-storage member causes movement to a second stable configuration, where the inner edge of the energy-storage member approaches the second horizontal plane and the outer edge of the energy-storage member approaches the first horizontal plane. In a sense, the relative positions of the inner rim and outer rim invert as the member transitions from a first to a second stable configuration, and back. In one embodiment, the force for movement from the first stable configuration to the second stable configuration is less that the force needed to move the member from the second stable configuration to the first stable configuration. In one embodiment, a force of at least 10% greater, preferably 20% greater, still more preferably 30% greater is needed to transition the member from its second stable configuration to its first stable configuration.

In a preferred embodiment, the energy-storage member as an axis of symmetry with an n-fold rotational symmetry for n, where n is an integer of 1, 2, 3, 4, 5, 6, 7, 8, 9, 10, 11, 12, 13, 14, 15, 16, 17, 18, 19 or 20. In a preferred embodiment, n is between 3-18, preferably between 3-12, still more preferably between 3-9. By way of example, the slotted spring embodiment of FIG. 1G has an axis of symmetry with a 9-fold rotational symmetry. The energy-storage member is stable in both its first and second configurations, wherein stable intends that the member does not transition between first and second configurations except upon application of external force. As noted above, in a preferred embodiment, the force to move from a second configuration to a first configuration is different, e.g., greater, than the force needed to move from a first configuration to a second configuration.

A skilled artisan will appreciate the wide variety of energy-storage members that would be suitable for use, and examples are illustrated in FIGS. 1H-1T. The embodiments shown, with the exception of FIGS. 1R and 1S, have an axis of symmetry. Several of the embodiments have an 9-fold rotational symmetry, for example, the embodiments of FIGS. 1K and 1L. Other embodiments have a 6-fold rotational symmetry, for example, the embodiments of FIGS. 1H, 1J, 1M and 1T. It is to be understood that other similar shapes, including but not limited to other axisymmetric shapes, may be used to create an energy-storage member with two stable configurations. Further, non-symmetric shapes may be used to create an energy-storage member with two stable configurations. It is also to be understood that the presence or absence, size, shape, and configuration of any slots or cutouts in the energy-storage member may be altered to allow the energy-storage member to have two stable configurations. It is also to be understood that the energy-storage member may comprise a plurality of individual energy-storage members that may or may not be identical in size, shape, and material. The usage of a plurality of individual energy-storage members is useful to allow alteration of applicator velocity, energy, activation force, or other performance characteristics in ways that may not be achievable with a single energy-storage member.

In operation, and with reference again to FIGS. 1A-1E, an applicator comprising an energy-storage element is placed in contact with the skin such that skin contacting element 12 is directly on the stratum corneum and, optionally, adhered to skin by means of adhesive disposed on element 12. The energy-storage element is in a first stable configuration and is movable to a second stable configuration by application of force. Actuating member 20 is pressed downward, in the direction of arrow 32. This causes actuating member 20 to move downward, engaging inner edge 30 of energy-storage member 28, and applying the force necessary to move the energy storage member into its second stable configuration, wherein the inner edge 30 of the member approaches the horizontal plane previously defined by the outer edge of the member (e.g., FIGS. 1E-1F). As a result of movement of the energy-storage member, a microarray in contact with holder 24 comes forcibly into contact with skin.

The process of inversion of energy storage member may be quite rapid, appearing for example instantaneously to the human eye. It may last, for example, no more than about 10 ms, no more than about 30 ms, or more than 100 ms, or no more than ½ second. The shape assumed by energy storage member following inversion may be the reflection of the original shape in a plane.

The material from which the energy storage member is manufactured is variable, and a skilled artisan will appreciate that it is selected based on the several design considerations, including storage life and desired application force, which of course will also depend on the configuration of the member. Exemplary materials include metals, alloys, plastics, and specific examples include stainless steel and thermoplastics.

Figure 2A:
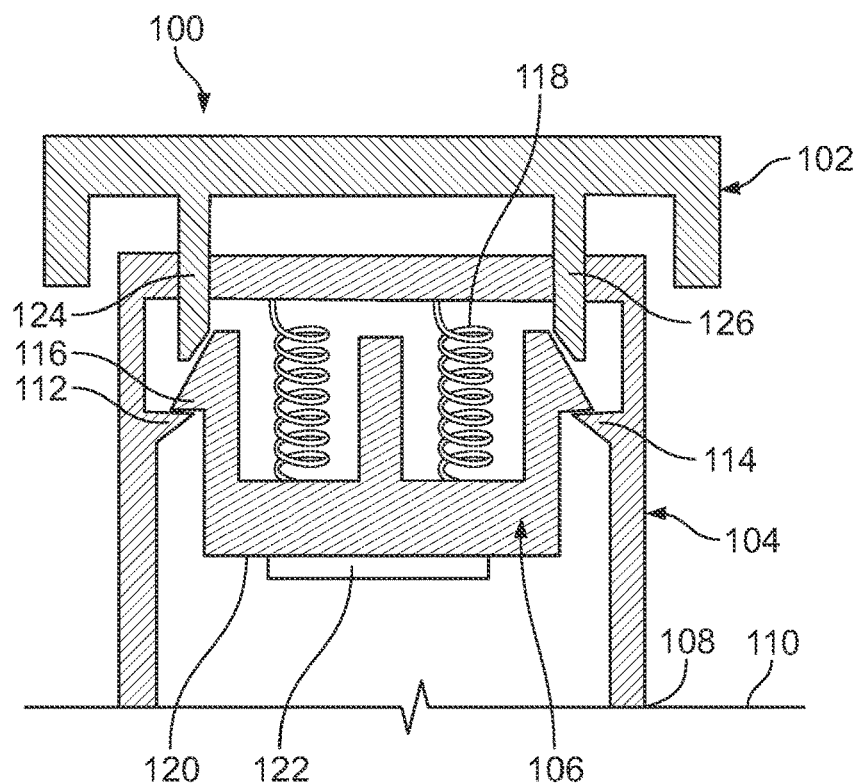
FIG. 2A depicts schematically, with certain dimensions exaggerated for clarity, an applicator.

FIG. 2A depicts schematically in cross-section, with certain dimensions exaggerated for emphasis, another embodiment of an applicator, prior to actuation. Applicator 100 comprises three principal members, an actuator 102, a housing 104, and a push member 106. Housing 104 comprises a distal edge 108 contoured for contact with skin 110. Housing 104 also has at least two projections extending from its inner circumferential surface, such as projections 112, 114. In other embodiments, the number of projections is 3, 4, 5, 6, 7, 8 or more. Each projection mates with a matching projection that extends from push member 106, where FIG. 2 shows matching projection 116 mating with projection 112. Collectively the projections hold push member 106 and resist the force of a spring 118 tending to push the push member 106 down. Member 106 has a planar base surface 120 onto which a microprojection array 122 is affixable or affixed.

In order to cause member 106 and the attached microprojection array 122 to be driven towards the skin 110, it is necessary to dislodge member 106 from the projections such as 112 and 114. In order to do that, actuating member 102 is used. It contains for each of the projections such as 112 and 114 a rod, such as rods 124, 126. The rod by pressing down on the matching projections causes the projection to flex inward and to escape from contact with its matching projection, such as matching projections 112, 114. Having moved past those projections, member 106 is no longer held up by them, and the spring 118 is free to release its energy in order to move member 106 downward.

Figure 2B:
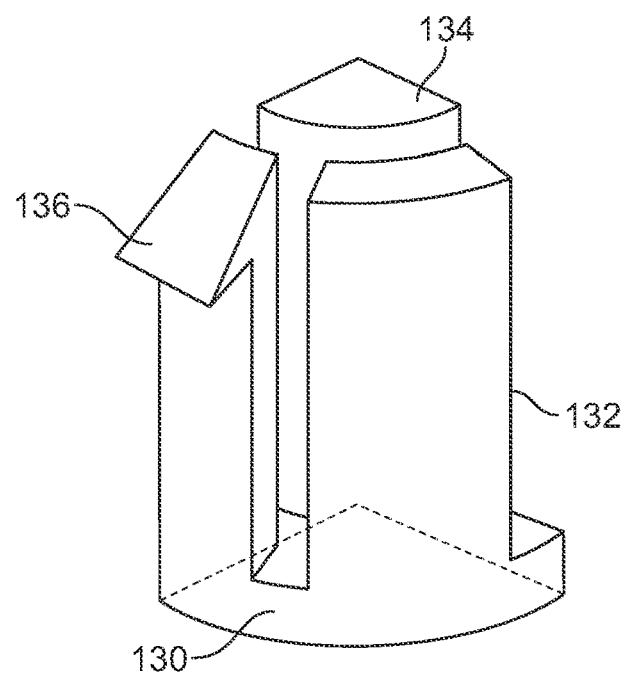
FIG. 2B depicts schematically, with certain dimensions exaggerated for clarity, one quarter of the push member of the applicator of FIG. 2A.

The structure of member 106 is further explained by FIG. 2B, which depicts schematically one quarter of member 106. It is seen that this quarter has a base 130, a wall 132, a central column 134 and a projection 136, which is designed to engage with a projection on the applicator housing, such as projection 112 seen in FIG. 2A.

In FIGS. 2A-2B as indicated above the dimensions are exaggerated for clarity. In reality the projections on members 104 and 106 might be smaller than depicted in the figures so as not to require so great a flex inwards when the actuation member 102 is pressed down. It would be expected that all three members 102, 104 and 106 would be composed primarily of flexible polymers or rigid polymers (including reinforced polymers). Possible materials include polycarbonate, polyetheretherketone (PEEK), polyethylene, polypropylene, polyethylene terephthalate, or other polymeric material. Fillers added to the polymer during manufacture can include glass fibers, Kevlar fibers, aramid fibers, metal fibers, carbon fibers or other polymeric filler material. These filler materials serve the purpose of carrying additional loads within the polymeric matrix such that the mechanical loading experienced by the polymer in the applicator parts is distributed between the polymer itself, and the filler. The use of fillers within the polymer reduces the dimensional distortion on the applicator parts if they experience any mechanical loading. The polymer and fillers also minimize creep due to less force experienced by the polymer itself. Reducing the dimensional distortion and creep lead to maintaining the same stored elastic energy for an extended period of time. Maintaining the same stored elastic energy over a period of time is important for having an extended shelf life of preferably at least 6 months, more preferably 12 months, and most preferable 24 months. These materials and characteristics described herein may also be used for other parts of the applicator to increase mechanical strength and stability, and reduce dimensional distortion and creep.

Many variations on FIG. 2A are possible. For example, the number n of projections like 112 and 114 around the inner periphery of member 104 could be varied. They would generally be expected to be placed at positions 360/n degrees apart, but it might be desired to space them more closely in some instances, for example with four projections at 0 degrees, 80 degrees, 180 degrees, and 260 degrees.

The skin-contacting edge 108 of housing 104 could be provided with a skirt so that the area which contacts the skin is more extensive. The skin-contacting edge could be provided with an adhesive, which in turn would in storage conveniently be covered by an optional release liner.

In the device of FIGS. 2A-2B, the energy needed to actuate is that required to flex inward the projections, such as projections 116 (FIG. 2A) or 136 (FIG. 2B) of member 106. This energy depends on their precise dimensions and the material characteristics (e.g., Young's modulus) of the material out of which they are made. If this pressure were sufficiently low that inadvertent actuation were a possibility, it might be desirable to place some kind of spring or spring-like object between the actuating member and the push member, so that an energy needed to deform this object must be supplied before actuation can occur. The use of such an object allows the user input force to be set at a level suitable for the target population without imposing limitations on the energy stored in the spring used to propel the microneedle array.

In further variants on the design of FIGS. 2A-2B it is possible to use features in addition to or different from the projections to hold a push member and spring in place prior to actuation. A design of this type is depicted in FIGS. 3A-3B.

Figure 3A:
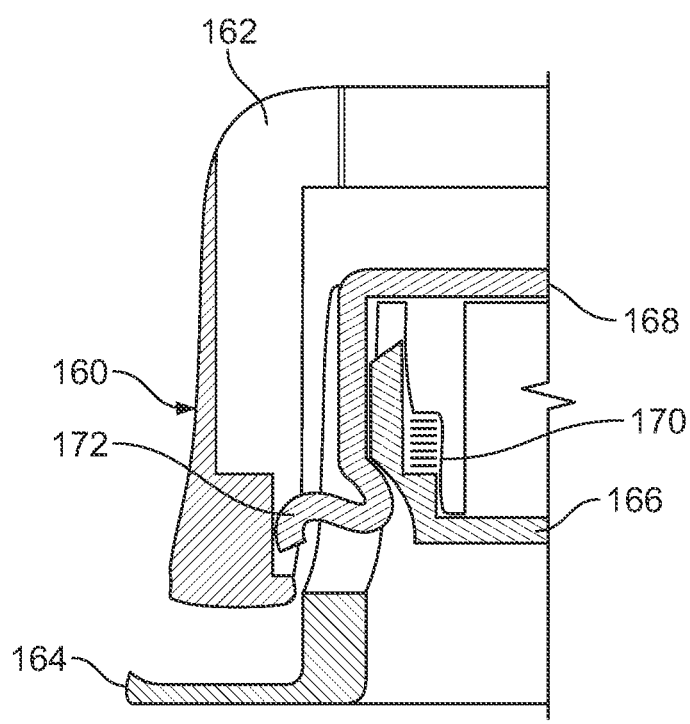
FIGS. 3A-3B depict schematically another embodiment of an applicator, where in FIG. 3A a schematic cross-section of one half of the applicator is shown, and in FIG. 3B a perspective view of a particular component is shown.
Figure 3B:
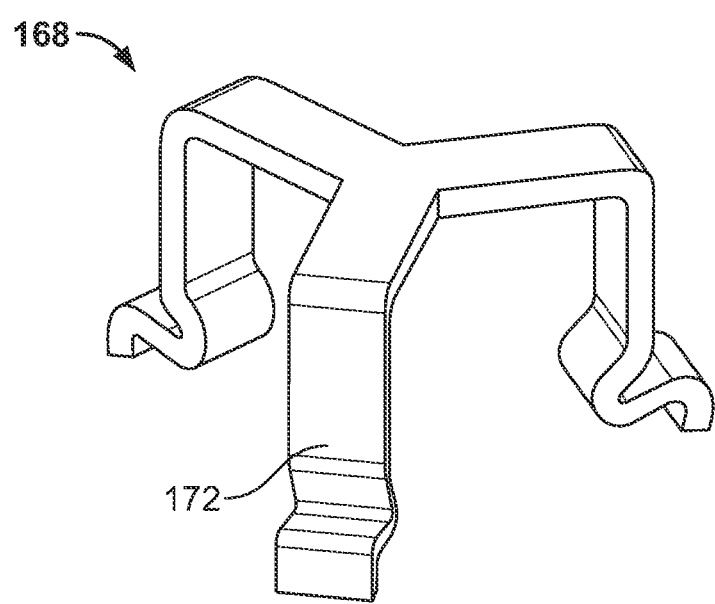

In FIG. 3A, which is a schematic cross-section, is a member 164 which makes contact with skin. Engaged with member 164 is a clip 168, which is depicted also in perspective in FIG. 3B. Clip 168 has a certain number of outward projections, such as projection 172. In the embodiment shown, there are three such outward projections. These outward projections may generally flex in an approximately radial direction towards the center of clip 168. These outward projections fit into openings in member 164 as shown in FIG. 3A. Underneath member 164 there is a further member 166 which holds a microprojection array (which is not shown in the figure). Between members 164 and 166 is a spring 170. Spring 170 serves as an energy-storing member. It tends to push member 166 downward. However, it is restrained by the projections like 172 of clip 168.

In contact with clip 168 is an actuation member 160. It has openings like 162, one for each of the outward projections like 172. The lower portions of these openings like 162 have a surface against which the projections like 172 press during storage. However, when actuation member 160 is pushed downwards, eventually the projections like 172 are enabled to flex outwards, releasing member 166 and allowing spring 170 to push member 166 downwards towards the skin.

Springs of different kinds (not shown in FIG. 3A) may be used to establish a minimum force which is necessary to push down member 160 and actuate the applicator. Such springs may, for example, be located between the upper surface of member 164 and the lower (inner) surface of actuation member 160.

The clip 168 may be made of metal, while the remainder of the applicator is made of suitable polymers. By making the clip of metal, the vertical wall of the housing may be made thinner, a thick section on that wall not being needed to avoid creep. As may be seen from the description above, the projections 172 in this embodiment extend further outward than the position shown in FIG. 3A, so that some force is required to push them in enough to fit the bottom of the opening 162 in housing 160 as shown in FIG. 3A.

Figure 4A:
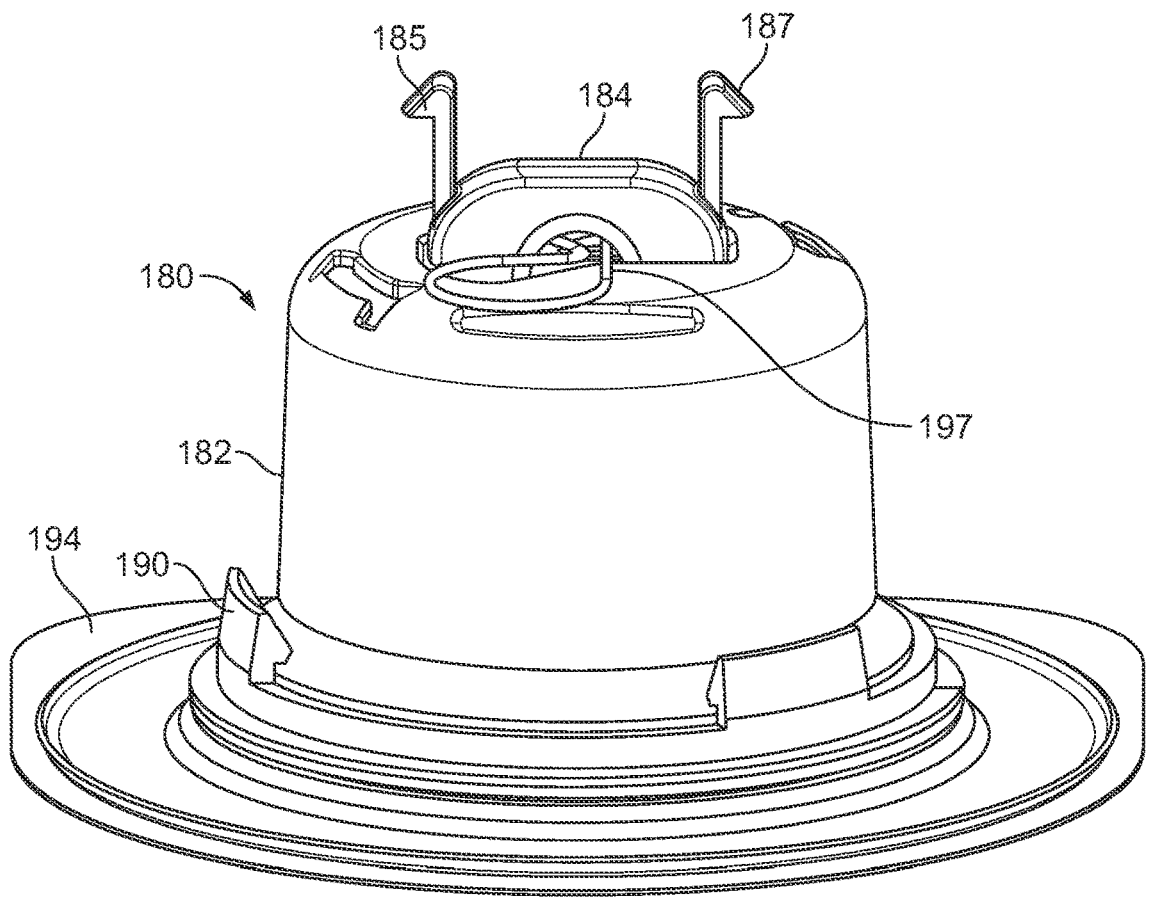
FIG. 4A shows an exploded view of another embodiment of an applicator.
Figure 4B:
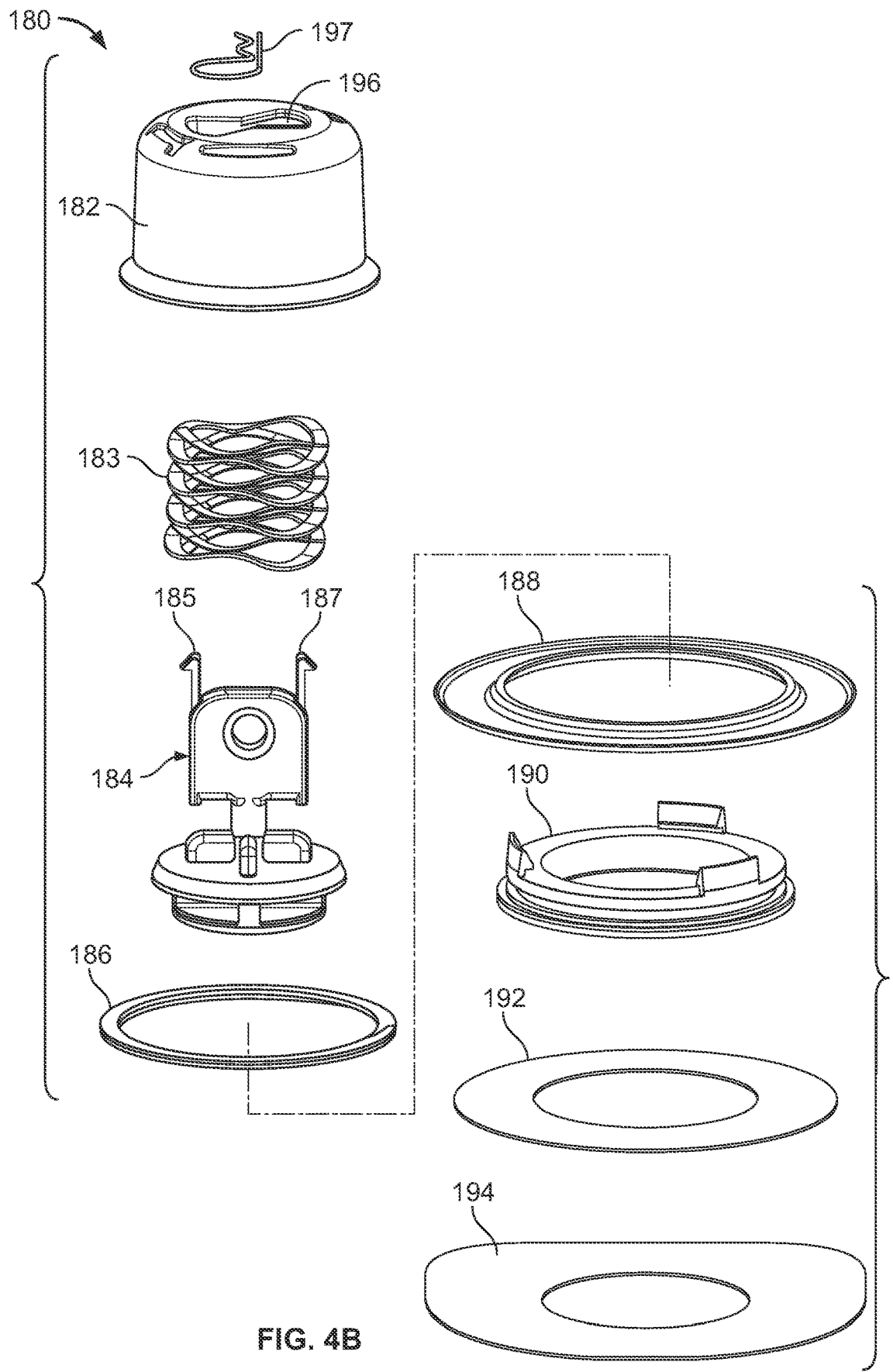
FIG. 4B shows a perspective view of the same applicator.

FIGS. 4A-4B schematically disclose another embodiment of an applicator 180, shown fully assembled in FIG. 4A and in exploded view in FIG. 4B. An outer housing 182 is separated by an energy-storage member 183 from a microprojection-holding member 184 which holds a microprojection array (not shown in the figure). In this embodiment, the energy-storage member is in the form of a wave spring, as illustrated in FIG. 4B. A wave spring is preferred in some embodiments over other types of compressive springs due to its small size when compressed, which is of value for a disposable device. It is to be understood that other compressive springs are also suitable and the applicator of this embodiment is not limited to a wave spring. In storage, microprojection-holding member 184 is held in place by two platforms in housing 182, such as platform 196, against which a projection member, such as members 185, 187 in member 184, engages. When it is desired to activate the device, a user twists member 184 (e.g., with thumb and forefingers gripping projection members 185, 187) so that it is no longer over the platforms and restrained by them. When that twisting occurs, member 184 moves downward pressing the microprojections against the skin.

The applicator of FIGS. 4A-4B is further provided with a set of components for adapting to skin, in this case an adapter 190, a snap ring 186, and an extender 188. This extender has the same function as the outwardly projecting flange seen in FIG. 3A as part of member 164. In addition, FIG. 4A shows an adhesive 192 and a release liner 194. These kinds of components may also be used in connection with the other applicators described herein. The applicator of FIGS. 4A-4B also includes an optional safety feature, in this embodiment in the form of a pin 197 that is removably inserted through a cavity in microprojection holding member 184 prior to use. To enable the applicator for actuation, a user pulls pin 197 from its retaining position as shown in FIG. 4A to permit a user to activate the applicator by the twisting motion described above.

In an alternative embodiment of the applicators of FIGS. 4A-4B, the extender 188 of the applicator may have a frustoconical rather than a flat shape.

Figure 5:
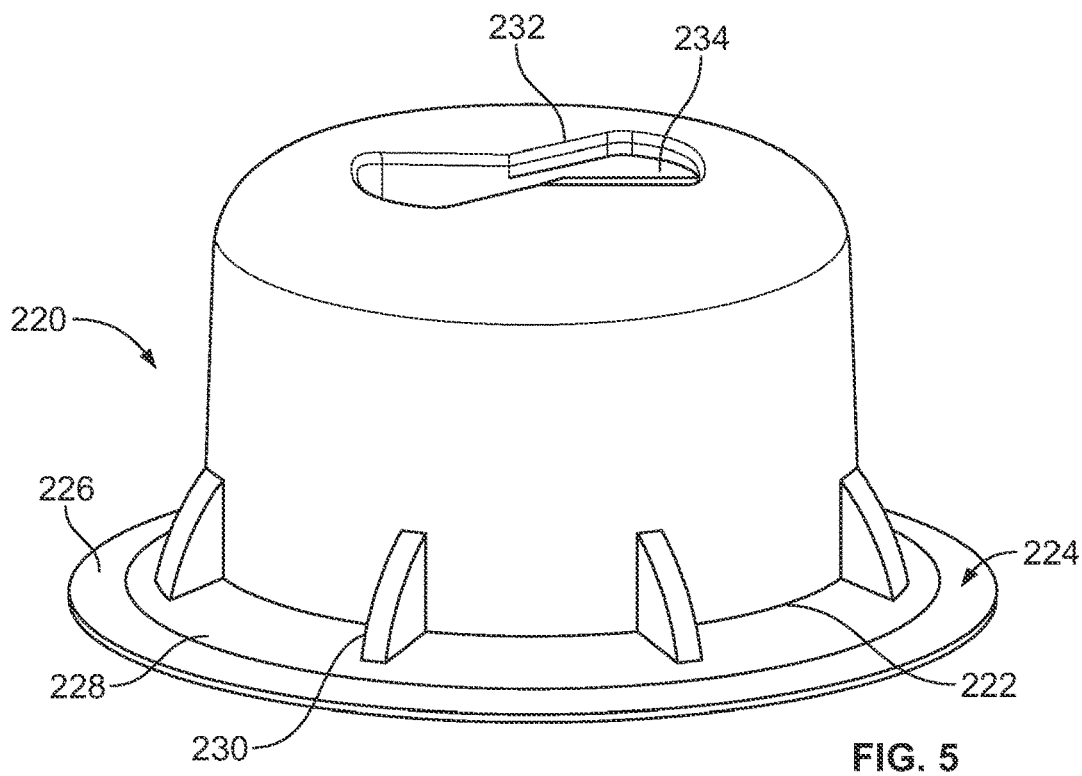
FIG. 5 depicts an alternative outer member for the applicator of FIGS. 4A-4B.

In another embodiment of the applicator of FIGS. 4A-4B, the housing member may be provided with its own outward projection for adaptation to skin, as depicted in FIG. 5. In FIG. 5, housing 220 comprises a base surface 222 with a projection 224 designed for contact with skin when in use. An outer portion 226 of the projection 224 has a thickness less than an inner portion 228. Reinforcing elements, such as element 230, are provided. Just as in FIGS. 4A-4B, there is an elongated opening 232 at the top of housing 220, where the opening comprises two platforms, such as platform 234, against which the microprojection-holding member presses when the applicator is in storage.

A feature of merit for applicators is the skin penetration efficiency achieved with a particular microprojection array. An exemplary test for skin penetration efficiency requires the placement of the microneedle array upon a test sample of cadaver skin, the insertion of the array the applicator under testing, and the withdrawal of the array after a period of time. At that time the percentage of openings in the skin sample that are deemed to allow adequate transport of material may be taken as a figure of merit. A material that may be used to test adequacy of transport is India ink. It is desirable that at least about 80%, preferably at least about 90%, and more preferably at least about 95% of the openings in the skin allow adequate transport of material.

The applicators described herein above can optionally include a safety mechanism or latch to prevent unintended actuation of the applicator and consequential deployment of the microneedle array. Various embodiments of a safety mechanism are now described.

Figure 6A:
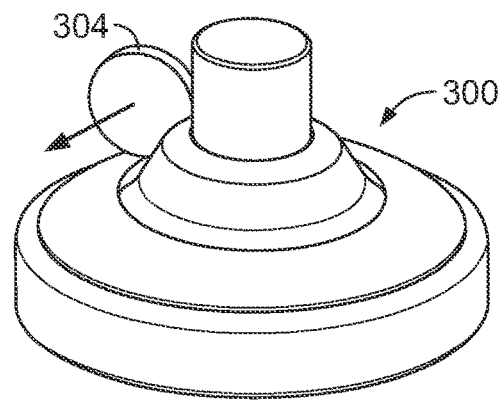
FIGS. 6A-6B illustrate a cantilevered pin safety mechanism to prevent unintentional deployment of an activator.
Figure 6B:
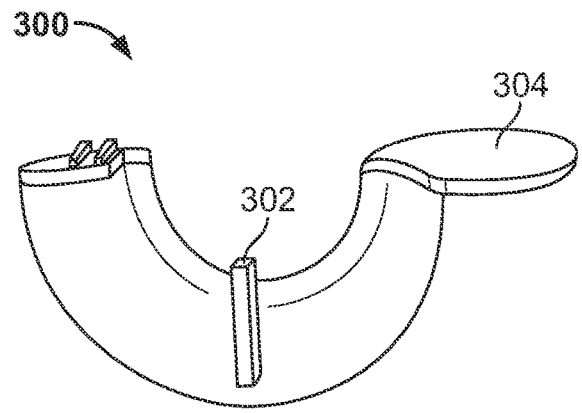

In a first embodiment, a pin or tab is used to prevent accidental actuation of the applicator. By way of example, FIGS. 6A-6B illustrate a cantilevered pin safety mechanism, where a retaining member 300 is dimensioned to snap fit on an applicator housing. Retaining member 300 is shown in FIG. 6A positioned on an applicator housing, and is shown alone in an enlarged side view in FIG. 6B. One or more pins, such as pin 302, on the retaining member fit within a groove in the actuation member of an applicator, preventing deployment of the actuation member. Rotation of the retaining member in a clockwise or counterclockwise direction by pressing on tab 304 releases the pin from the retaining groove, to allow deployment of the actuation member.

Figure 7A:
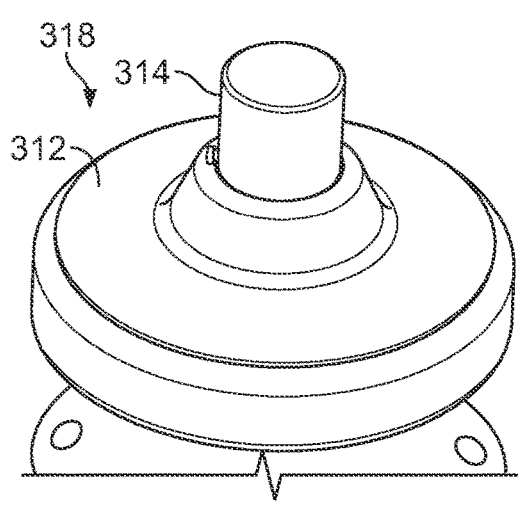
FIGS. 7A-7B illustrate another embodiment of a safety mechanism to prevent unintentional deployment of an activator.
Figure 7B:
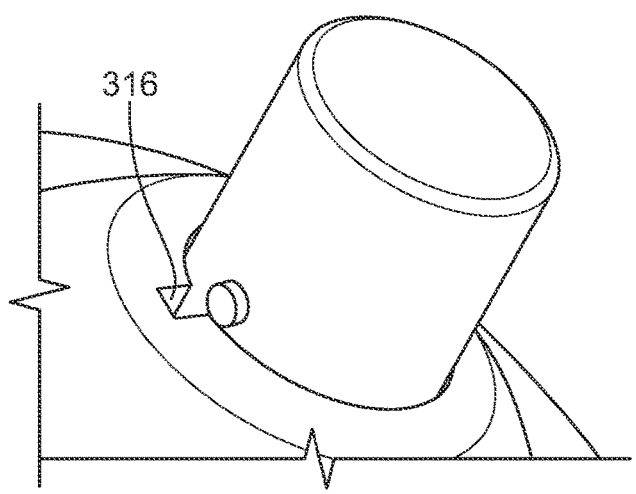

Another example of a pin-type safety mechanism is illustrated in FIGS. 7A-7B. Applicator 310 comprises a housing 312 and an actuation member 314 movably inserted into an opening in housing 312. A slot 316 is formed in actuation member 314 at a position where the slot is in movable engagement with a pin 318. When the pin is fully seated in the slot, actuation member 314 is in a locked position. A twisting motion of the housing or the actuation member unlocks the pin and slot, so that the actuation member can be deployed.

Figure 8A:
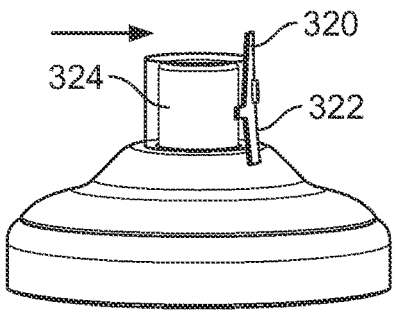
FIGS. 8A-8B illustrate an example of tab safety mechanisms to avoid accidental actuation of an actuation member in an applicator.
Figure 8B:
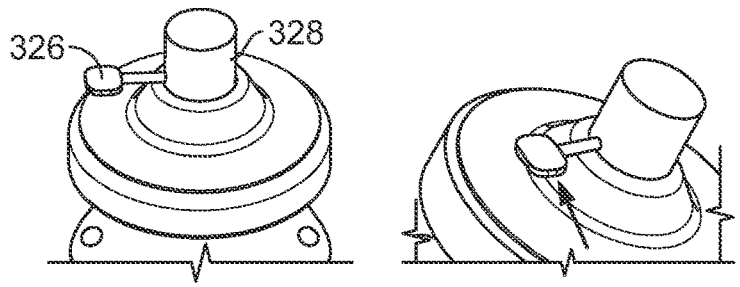

FIGS. 8A-8B illustrate other examples of tab safety mechanisms, where in FIG. 8A a cantilevered push tab 320 is movable to displace a pin 322 that locks an actuation member 324 in place. FIG. 8B shows a twist tab or snap tab 326 that interferes with movement of the actuation member 328. Removing the twist tab by twisting until it breaks off releases the safety mechanism and allows actuation of the applicator.

Figure 9A:
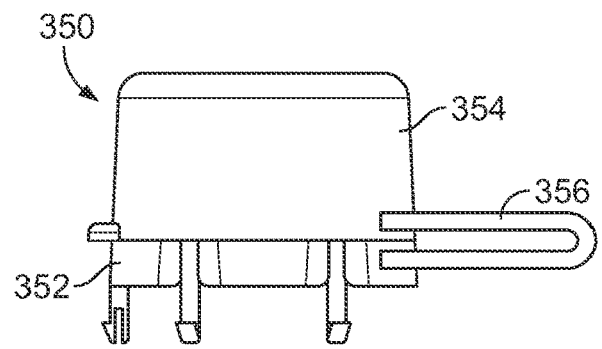
FIGS. 9A-9C illustrate another embodiment of a safety mechanism, where a protective cap is shown in a closed position (FIG. 9A) and in an open position (FIG. 9B), and disposed in place on an applicator (FIG. 9C).
Figure 9B:
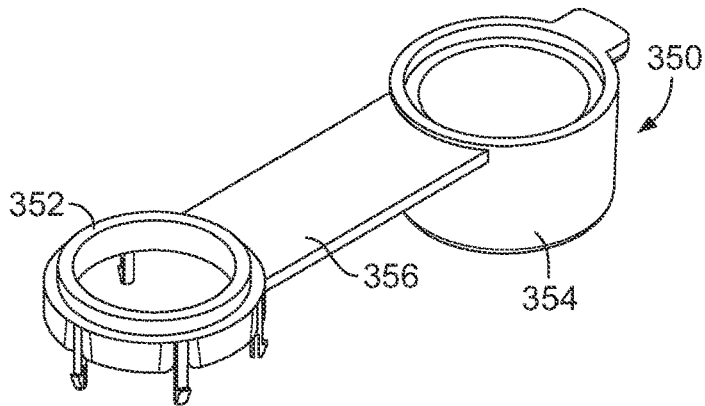
Figure 9C:
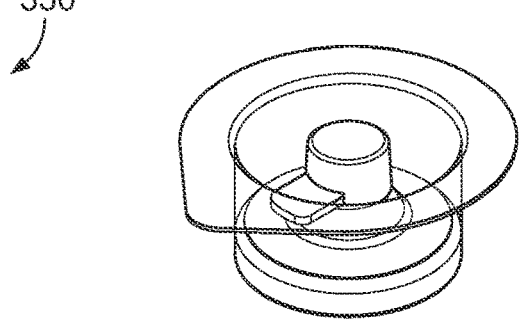

In a second embodiment, a safety mechanism in the form of a protective cap is provided, to prevent inadvertent actuation of an applicator comprising a microneedle array. An example is provided in FIGS. 9A-9B, where cap 350 is shown in a closed position (FIG. 9A) and in an open position (FIG. 9B). Cap 350 comprises a retaining member 352 and a cup member 354 connected to the retaining member by a flexible bridge member 356. Barbs or hooks extend from the retaining member, to fix the cap onto an applicator, as depicted in FIG. 9B. The cup member shields an actuation member on the applicator, preventing inadvertent application of force to the actuation member, and consequential deployment of the microneedle array.

Figure 10A:
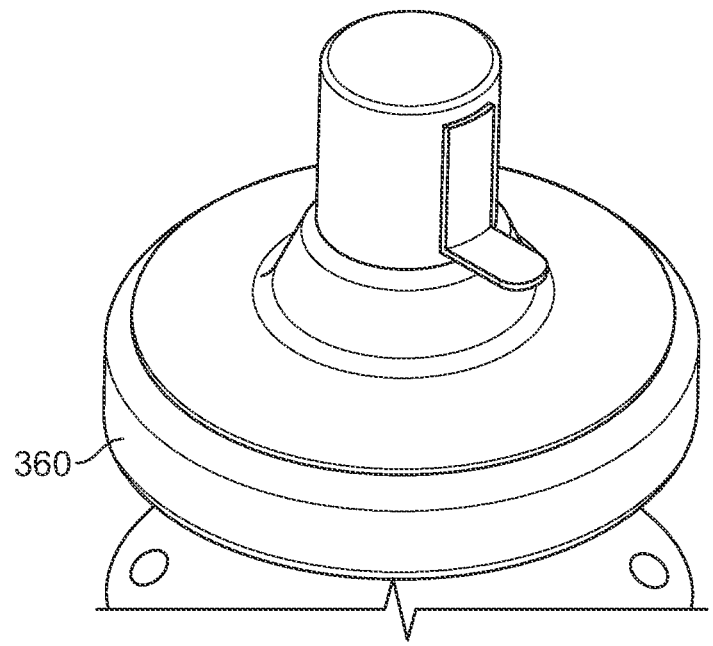
FIGS. 10A-10B illustrate another embodiment of a cap type safety mechanism.
Figure 10B:
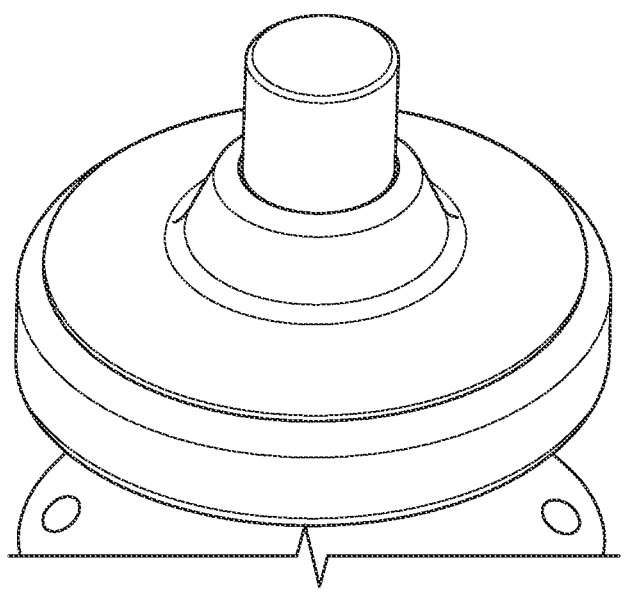

FIGS. 10A-10B illustrate another embodiment of a cap type safety mechanism, where a peel cap 360 fits snugly about the outer periphery of an applicator, preventing access to the actuation member of the applicator. Removal of the peel cap exposes the actuation member, rendering it available for use.

Figure 11A:
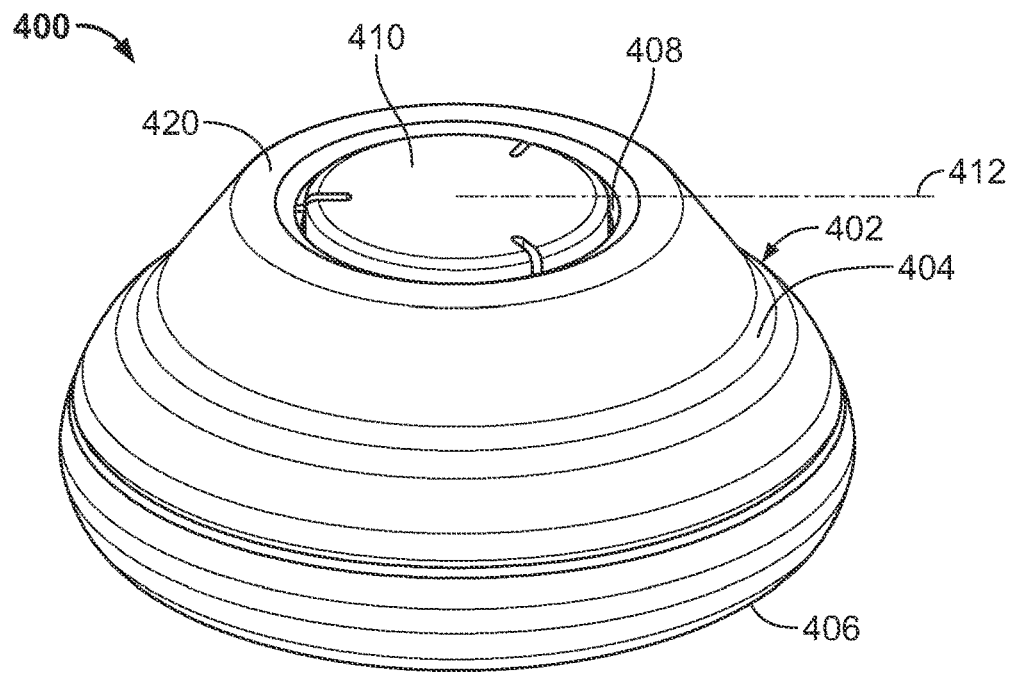
Figure 11B:
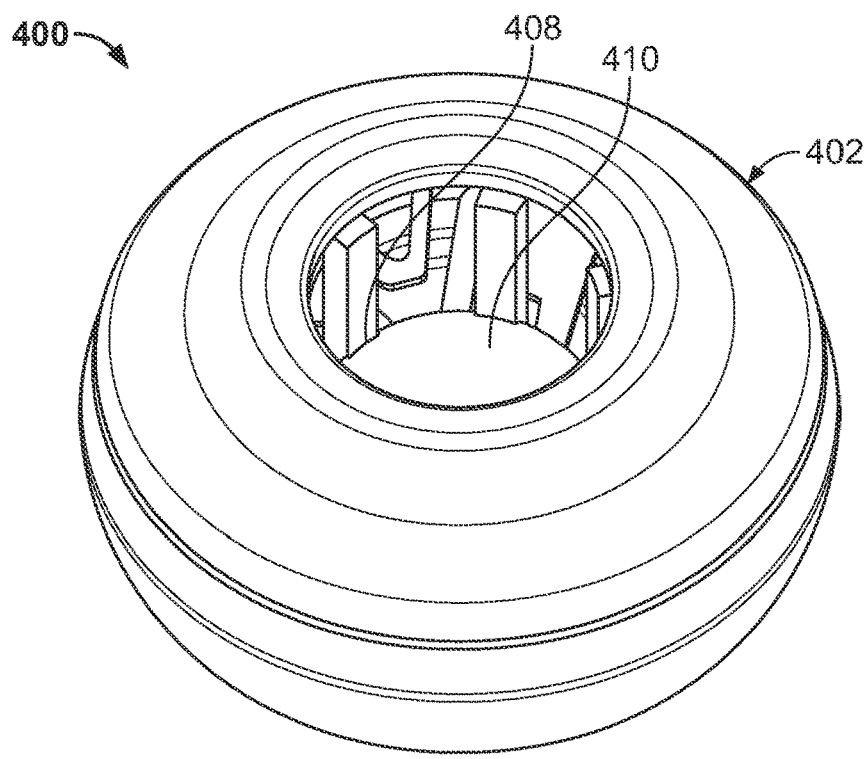

In another embodiment, the applicator described herein is designed to prevent unintended actuation of the applicator and consequential deployment of the microneedle array in accord with the design depicted in FIGS. 11A-11B. FIG. 11A depicts an applicator 400 in a configuration prior to deployment or actuation by a user. FIG. 11B depicts the same applicator after deployment or actuation by a user. Applicator 400 is comprised of a rigid housing 402 comprised of a first member 404 and a second member 406. In other embodiment, the housing is semi-rigid, semi-flexible, or flexible. First and second members are configured to engage one another so as to fit together in a secure configuration, such as by a snap-fit mechanism or an insertable lip/groove mechanism (seen, for example, in FIG. 12A). First member or upper housing member 404 has a central opening 408 in which an actuating member 410 slidingly fits. Second member or skin contacting member 406 is hollow or open, to receive the actuating member upon actuation of the applicator, as seen in FIG. 11B. Prior to actuation of the application (FIG. 11A), the plane of the top surface of actuating member, denoted by dashed line 412 in FIG. 11A, is co-planar or slightly under/lower than the plane of the uppermost edge of the first member 404 of housing 402, denoted by dashed line 414 in FIGS. 12A-12B, which are cross-sectional views of an exemplary applicator. In this configuration, the external, upper surface of the actuating member is co-planar with the uppermost surface of the housing, so that the actuating member is nested into or recessed into the housing prior to its actuation. After actuation of the actuating member, wherein the actuating member is deployed to a second position, the actuating member is depressed into the housing and the upper surface of the actuating member approaches a plane defined by an upper rim of the second housing member 406, denoted by dashed line 416 in FIGS. 12A-12B. As can be appreciated, the design wherein the actuating member is nested into the housing prior to actuation (e.g., the actuating member does not extend outward from the housing) prevents inadvertent deployment of the applicator.

The internal components of an applicator wherein the actuating member's upper external surface is flush with the uppermost (proximal with respect to the skin contacting surface of the housing) surface of housing can vary, and two embodiments are shown in FIGS. 12A-12B and FIGS. 13A-13B, wherein like elements with respect to FIGS. 11A-11B are given like numerical identifiers despite FIGS. 12A-12B and FIGS. 13A-13B being different embodiments.

Figure 12A:
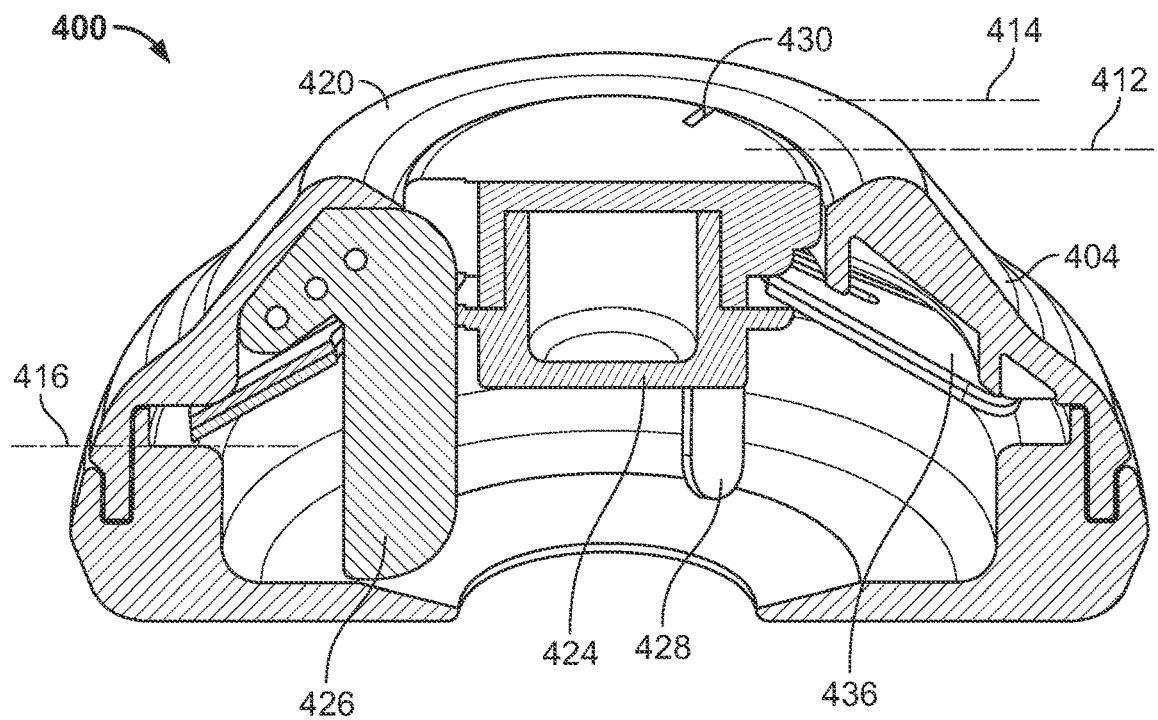
Figure 12B:
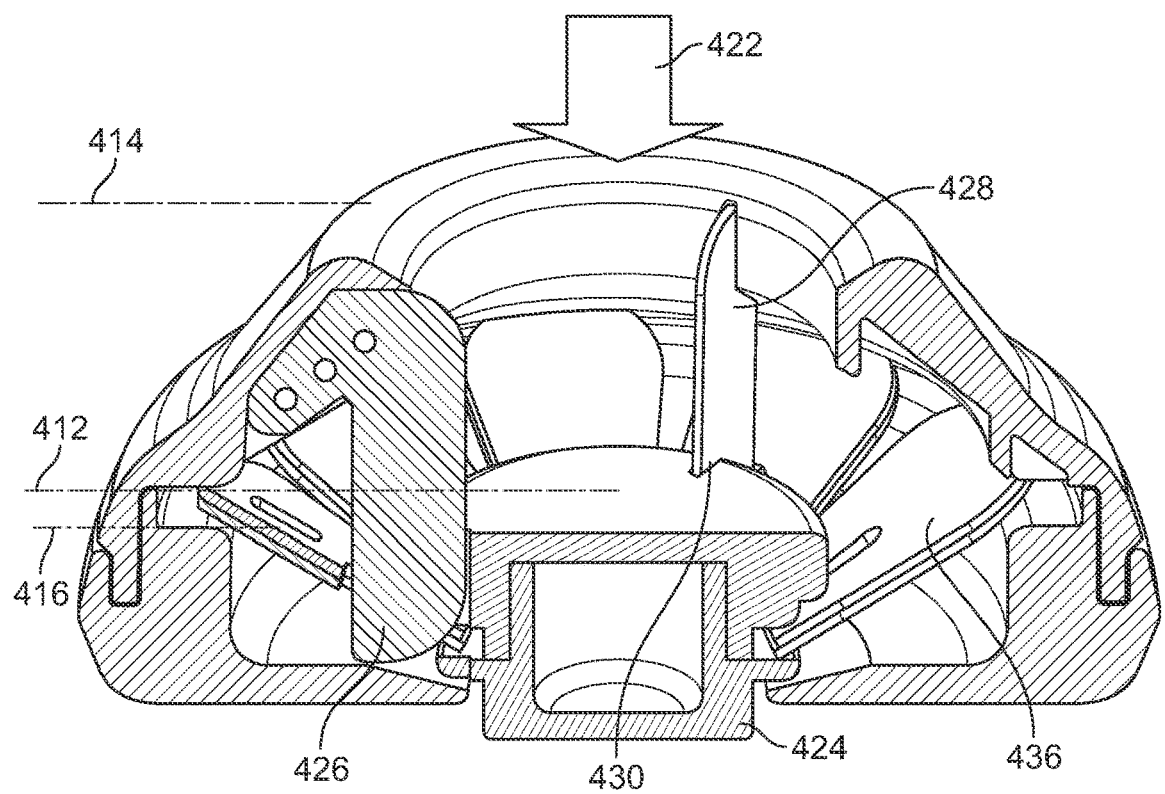

In FIGS. 12A-12B, applicator 400 is shown in a side cross-sectional view. First member 404 of housing 402 has an upper rim 420 that defines an uppermost plane of the applicator, the upper plane denoted by the dashed line 414. Actuating member 410 is movably positioned in the housing, movable between first and second positions, where in its first position the upper surface of the actuating member, denoted by the plane indicated by dashed line 412, is co-planar with the upper plane of the applicator or is slightly lower than the upper plane of the applicator, as seen in FIG. 12A. Upon application of a force, depicted by arrow 422, by a user, the actuating member travels to its second position, for deployment into the skin of a user of a microneedle array (not shown) positioned on a holding member 424 engaged with the actuating member. In its second, deployed position, the upper surface of the actuating member approaches, contacts, or travels beyond, a plane defined by an upper rim of the second housing member 406, the plane denoted by dashed line 416.

With continuing reference to FIGS. 12A-12B, actuating member 410 travels from its first to second positions along a plurality of guide fins, such as fins 426, 428. A groove for each guide fin, such as groove 430, is disposed in actuating member. Grooves or slots are similarly provided in the first and second members of the housing, to secure each guide fin in the applicator. The plurality of guide fins guide the plunger of the actuating member relative to the housing to maintain alignment during activation of the device. Each guide fin is dimensioned with sufficient thickness to avoid sharp edges, and the edges can be curved with a radius of curvature to ensure no sharp edging. It is also desirable that each guide fin have a horizontal axis of symmetry that allows for its insertion into the housing in either direction.

Figure 13A:
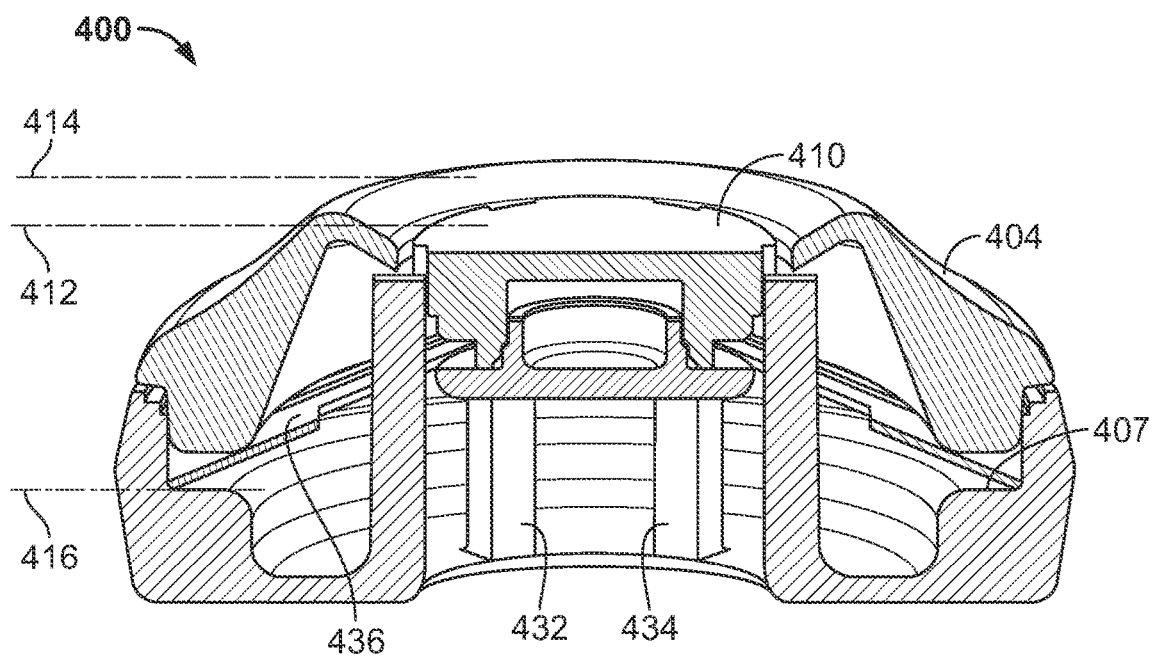
Figure 13B:
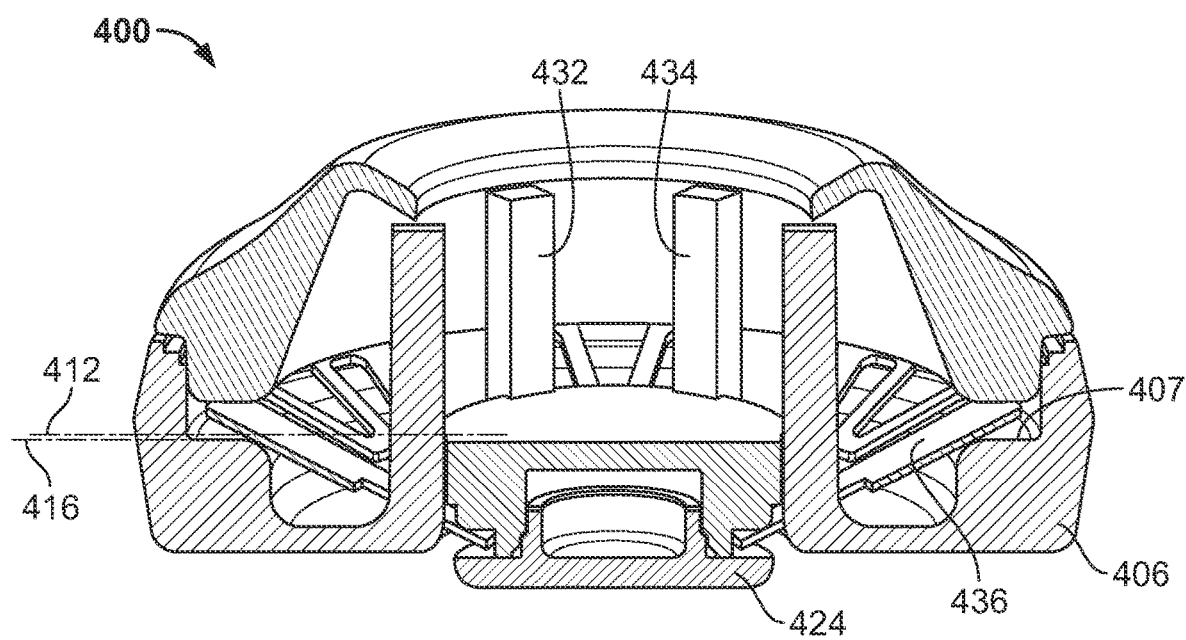

FIGS. 13A-13B are cross-sectional side views of another embodiment of the applicator of FIGS. 11A-11B, wherein FIG. 13A shows the applicator prior to activation and FIG. 13B shows the applicator after its activation. In this embodiment, the applicator prior to activation has an actuating member 410 that is recessed within the housing, as evident from the fact that the upper surface of the actuating member is below or under the upper rim of the first housing member 404, as illustrated by the respective dashed lines 412 (corresponding to the plane defined by the upper surface of the actuating member) and 414 (corresponding to the plane defined by the plane defined by upper rim of the first housing member). As seen in FIG. 13B, activation of the actuating member by application of a force moves the actuating member to its second position, wherein the upper surface of the actuating member is closer (relative to the upper surface of the actuating member in its first position) to the upper rim 407 of the second housing member 406, denoted by dashed line 416. The actuating member travels from its first to second positions along a plurality of guide posts, such as posts 432, 434. The guide posts extend from the first member of the housing to the second member of the housing, and are affixed to the each member. The outer circumference of the actuating member contacts each of the guide posts, which serve to guide the actuating member relative to the housing during movement of the actuating member.

FIGS. 12A-12B and 13A-13B also illustrate the energy storage element 436 positioned with the applicator. As discussed in detail above, the energy storage element moves from a first position to a second position upon application of a force by the actuating member. Movement from its first to its second position occurs only upon application of a sufficient force, and results in an inversion of the element. The element is stable in both its first and second positions in that it does not of its own accord move between the positions, but requires application of force to move from its first to its second position, and from its second position to its first position. In a preferred embodiment, the force required to move the element from its second to its first position is less than the force required to move the element from its first to its second position. Absent application of force, the element cannot return to its first position subsequent to actuation of the device. Prior to activation of the applicator, the energy storage element contacts the second housing member that is in contact with the skin, and after activation, the energy storage element is in contact with the first member of the housing (also referred to as an outer cover). Activation of the actuation member releases energy stored in the energy storage element, the release energy acting on the microprojection holding member in contact with the actuating member.

Methods of Use

In another aspect, a method for administering an active agent to a subject is provided. The method comprises providing a microprojection array in conjunction with any one of the applicators described herein, the microprojection array comprising an active agent. The agent is delivered transdermally by actuation of the applicator, to deploy the microprojection array into contact with the skin, or more generally a membrane or body surface, of a subject. The active agent to be administered can be one or more of any of the active agents known in the art, and include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In preferred embodiments is a protein or a peptide. In another embodiment, the agent is a vaccine. Example 1 below details administration of human parathyroid hormone to porcine skin in vitro. Examples 2-4 detail administration of human parathyroid hormone to human subjects. Additional details of administration of human parathyroid hormone to human subjects using a microprojection array, including detailed pharmacokinetic analysis, are given in provisional application No. 61/331,226, filed May 4, 2010; the entire contents of this co-filed application are incorporated by reference herein. Additional examples of peptides and proteins which may be used with microneedle arrays are oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides are also contemplated, and include DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

It is to be understood that while the subject matter has been described in conjunction with the preferred specific embodiments thereof, the foregoing description is intended to illustrate and not limiting in scope. Other aspects, advantages, and modifications will be apparent to those skilled in the art to which the subject matter pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLES

The following examples are put forth so as to provide those of ordinary skill in the art with a complete disclosure and description of how to make and use the subject matters described herein, and are not intended to limiting in the scope of the subject matter. Unless indicated otherwise, parts are parts by weight, temperature is in ° C. and pressure is at or near atmospheric.

Example 1

Comparative Testing of Applicators

Three slotted spring applicators designated B1, B2 and B3, similar to those depicted in FIGS. 1A-1F, were compared with an applicator designated "A" of the type depicted in FIGS. 4A-4B for skin penetration efficiency and ability to deliver hPTH(1-34) (human parathyroid hormone 1-34 fragment, also referred to as teriparatide when produced recombinantly). The applicators B1, B2 and B3 differed in the precise characteristics of the slotted spring energy-storing element (dimensions and material). Applicator B1 was 0.012 inches thick stainless steel, Applicator B2 was 0.0155 inches thick and made of 17-7 stainless steel, and Applicator B3 was 0.0155 inches thick and made of 301 stainless steel. The B1 slotted springs had somewhat longer indentations from the outside in comparison to the B2 and B3 slotted springs.

Microprojection arrays were fabricated from Dextran-70 and containing hPTH(1-34), as described in U.S. Publication No. 2008-0269685. The sequence of hPTH(1-34) used was:
H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (SEQ ID NO:1)

The microneedles were 4-sided pyramids with spacing 200 µm, microneedle height 250 µm, and array diameter 11 mm, with 2742 microneedles per array.

Testing was done with porcine skin smoothed flat on a polyurethane foam backing. The apparent dose delivered was determined by analyzing the residual amount of hPTH (1-34) in the arrays and on skin. Results are shown in the table.

| Device | | | Apparent Dose | | | % Delivery Efficiency | | |
|---|---|---|---|---|---|---|---|---|
| ID | Rep # | % SPE[1] | µg | Mean | SD | % | Mean | SD |
| A | Rep 1 | 94.3 | 32.4 | 32.0 | 0.6 | 86.4 | 85.2 | 1.7 |
|   | Rep 2 | 98.9 | 31.5 |      |     | 84.0 |      |     |
| B1 | Rep 1 | 83.3 | 18.9 | 23.0 | 5.7 | 50.4 | 61.3 | 15.1 |
|   | Rep 2 | 90.4 | 17.4 |      |     | 46.4 |      |     |
|   | Rep 3 | 96.9 | 26.7 |      |     | 71.2 |      |     |
|   | Rep 4 | 93.7 | 28.9 |      |     | 77.1 |      |     |
| B2 | Rep 1 | 99.9 | 18.5 | 27.7 | 6.2 | 49.3 | 73.7 | 16.4 |
|   | Rep 2 | 101.1 | 30.2 |      |     | 80.5 |      |     |
|   | Rep 3 | 100 | 30.0 |      |     | 80.0 |      |     |
|   | Rep 4 | 99.5 | 31.9 |      |     | 85.1 |      |     |
| B3 | Rep 1 | 92.9 | 8.9 | 19.3 | 8.6 | 23.7 | 51.3 | 22.9 |
|   | Rep 2 | 100.8 | 27.0 |      |     | 72.0 |      |     |
|   | Rep 3 | 94.8 | 15.5 |      |     | 41.3 |      |     |
|   | Rep 4 | 96.4 | 25.6 |      |     | 68.3 |      |     |

[1]SPE = skin penetration efficiency

Skin penetration efficiency (SPE) is estimated by counting the number of holes in the microneedle-treated skin region relative to the number of microneedles on the array used to treat the skin. It is believed that certain weaker results for SPE, such as the first replication of the B1 applicator, could be due to a possible error installing the slotted spring upside down into the plastic housing.

Example 2

Preparation of a Two-Layer Microprojection Array Containing Human Parathyroid Hormone (Hpth(1-34))

A microprojection array containing a therapeutically effective amount of hPTH(1-34) (32 µgrams) was prepared for use in a Phase I clinical study as follows.

First, in describing generally the features of the microprojection array, the microprotrusions of the array can be characterized generally as comprising a DIT (drug-in-tip) layer and a "backing" layer. The DIT layer includes hPTH (1-34) in a water-soluble matrix. The sequence of hPTH(1-34) used is as follows:
H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (SEQ ID NO:1)

The tip of the microprojections is also referred to herein as the layer at the bottom-most portion of the tips or microprotrusions (i.e., proximal to the skin when placed upon the skin), also referred to herein as the "end portion" that is distal to the base of the array). The "backing" layer as referred to in certain of these examples, encompasses both the upper portion of the microprotrusions proximal to the base of the array as well as the base itself, where the base is the portion of the array that supports the tips. The backing layer comprises a biocompatible, non-water soluble matrix. In the instant array device, the material in the upper portion of the microprotrusions is the same as the base material itself, so that the non-water soluble matrix formulation is applied as a single layer to fill the mold atop the DIT layer.

The DIT layer of the microstructure array dissolves into the skin and contains the components provided in Table 2-1. Acetate was the counter-ion in the hPTH(1-34) drug substance.

TABLE 2-1

Composition of Drug-in-Tip Layer of hPTH(1-34) TDS

| Trade Name | Chemical Name of Ingredient | Quantity (μg/unit) | Range (μg/unit) | % w/w (of the microstructure array) |
|---|---|---|---|---|
| hPTH (1-34) | human Parathyroid hormone (1-34) | 32.0 | 25.6-38.4 | 12.8 |
| Dextran 70 | Dextran, 70,000 Dalton molecular weight | 160.0 | 128.0-192.0 | 58.6 |
| Sorbitol, N.F. | Sorbitol | 54.9 | 64.0-96.0 | 21.9 |
| Histidine | L-histidine | 0.14 | 0.11-0.17 | 0.1 |
| Histidine HCl | L-histidine hydrochloride | 0.73 | 0.58-0.88 | 0.3 |
| NA | Acetate | 2.5 | 2.0-3.0 | 1.0 |
| Total | | 250.27 | | 100.0 |

The backing portion or layer of the array was composed of poly(DL-lactide-co-glycolide), 75:25, ester terminated (Tradename: LACTEL®).

The ingredients forming the tip portion of the formulation (i.e., the DIT formulation) were dissolved in water, cast, and dried in a silicone mold containing microstructure cavities to form the drug-in-tips (DIT) structures. The water insoluble, biocompatible polymer, poly(DL-lactide-co-glycolide), 75:25, was dissolved in acetonitrile to provide the backing formulation which was then coated on top of the DIT layer in the silicone mold, and then dried. The solvent was removed from the backing (upper portion proximal to the base, and base) during processing and was limited to a level below the amounts recommended in ICH guidelines.

Example 3

Preparation of a Transdermal Delivery Device (TDS) Containing a Microprojection Array Containing Human Parathyroid Hormone (hPTH(1-34))

The final transdermal/microneedle delivery system product (sometimes abbreviated herein "TDS") was assembled and contained the microprojection array described above in Example 2. The product was designed to deliver a systemic dose of hPTH (1-34) across the stratum corneum barrier layer of the skin using an array of microstructures. The final TDS product was formed by the integration of two components, a plunger-array assembly containing drug product and an applicator assembly, where these two items were packaged separately and integrated at the clinical site (See Example 4 below for clinical data).

The microprojection array contained in the plunger-array assembly possesses an 11 millimeter diameter of approximately 2700 microstructures arranged in a hexagonal pattern. The plunger-array assembly consists of the microprojection array mounted to an array support member, in this case, as plastic plunger with an adhesive laminate. The plunger-array assembly was packaged inside a protective container and pouched in a dry nitrogen environment.

The applicator assembly includes a plastic shell or housing with skin contact adhesive and a release liner, an energy storage member (in this case, a metal spring) to provide the energy needed to accelerate the plunger-array assembly, and elements to hold these items together until assembly at the clinic with the plunger-array assembly. This unit is packaged inside a protective container and pouched.

The final assembled drug product consists of the plunger-array assembly which is inserted into the applicator assembly. The TDS is activated by compressing the spring and then twisting the plunger to lock and hold the compressed spring in place until use. When activated, the spring delivers the stored energy to the plunger causing it to accelerate and contact the skin. Upon contact with the skin, the microstructures penetrate past the stratum corneum, and the hPTH dissolves into the skin rapidly. Following actuation of the spring and delivery of hPTH, the device is removed and discarded. The applicator assembly and plunger-array assembly as well as the final assembled TDS product correspond to those shown in FIGS. 4A-4B.

Example 4

In-Vivo Study: Administration of Human Parathyroid Hormone, hPTH(1-34), Via A Microprojection Array Device in Healthy Human Subjects An open label, single dose, sequence randomized, 3-way cross-over study was carried out in sixteen healthy female volunteers to determine the pharmacokinetics (along with additional secondary endpoints) of 32 μg hPTH(1-34) and 64 μg hPTH(1-34) (32 μg hPTH(1-34)×2) delivered using the microneedle transdermal delivery system identified by the tradename MicroCor®, described in Examples 2 and 3 relative to subcutaneously administered (SC) hPTH (teriparatide) commercially available under the tradename FORTEO®, 20 μg. One subject was withdrawn after the first treatment due to difficulty in bleeds resulting from venous spasms. The product described in Examples 2 and 3 is referred to in this example generally as "MicroCor® hPTH (1-34)" or simply, "MicroCor®".

Subjects received a single dose of 32 μg hPTH(1-34) or 64 μg hPTH(1-34) (32 μg×2) by applying the MicroCor® device to an abdominal site for 5 minutes. Treatment with FORTEO® was accomplished by administration as a subcutaneous injection into the abdominal wall. Treatments were separated by a 48-hour washout period. The plasma sampling schedule was as follows: pre-treatment, 5, 10, 15, 20, 25, 30, 40, 50, 60, 75, 90, 120, 180, 240, 300, 360 minutes, and 24 hours post-treatment. Vital signs were monitored pre-treatment, and at 15 and 30 minutes, and 1, 2, 3, 4, 5, 6, 8, 10, 12, and 24 hours post-treatment. Adverse advents were monitored throughout the study. Additional assessments included (i) measurement of anti-PTH antibodies prior to first treatment and 2 weeks following last treatment, (ii) measurement of serum calcium, phosphorous, albumin, and protein at pre-treatment, and 1, 2, 3, 4, 5, 6, and 24 hours post-treatment, as well as (iii) MicroCor® adhesion. The following tables summarize study results.

TABLE 4-1

Local Skin Tolerability

| Symptoms | Observation | MicroCor® (N = 17; 49 applications) | FORTEO® (N = 16) |
|---|---|---|---|
| Evidence of bleeding | Yes | 0 | 1 (6.3%) |
| | No | 49 (100%) | 15 (93.7%) |
| Discomfort at application | None | 9 (18.4%) | 10 (62.5%) |
| | Mild | 31 (61.2%) | 5 (31.3%) |
| | Moderate | 10 (20.4%) | 1 (6.3%) |
| Discomfort pre-removal (MicroCor® only) | None | 26 (53.1%) | N/A |
| | Mild | 21 (42.9%) | |
| | Moderate | 2 (4.1%) | |
| Discomfort at removal (MicroCor® only) | None | 44 (89.8%) | N/A |
| | Mild | 5 (10.2%) | |

TABLE 4-2

Pharmacokinetic Results

| Parameter | MicroCor® 32 µg | MicroCor® 64 µg | FORTEO® |
|---|---|---|---|
| AUC/Dose (pg * min/mL * mcg) | 220 (n = 15) | 229 (n = 16) | 429 (n = 16) |
| $C_{max}$ (pg/mL) | 180 (n = 16) | 336 (n = 16) | 85 (n = 16) |
| $T_{max}$ (minutes) | 8.1 (n = 16) | 7.4 (n = 16) | 26.2 (n = 16) |
| $T_{1/2}$ (minutes) | 37.1 (n = 16) | 52.0 (n = 16) | 52 (n = 16) |
| Time to reach 50% of $C_{max}$ (plasma normalized), minutes | ~20 | ~20 | ~90 minutes |

Application of hPTH with the MicroCor® device demonstrated good skin tolerability. Skin effects were transient and well-tolerated, with mild to moderate erythema observed.

In terms of general safety, all treatment regimes were well-tolerated. No significant adverse events nor unexpected adverse events occurred. In fact, there was no difference in the overall treatment-related adverse events between application of the hPTH via the MicroCor® device and the Forteo®-based treatment. No significant changes were observed in serum calcium, and no anti-PTH antibodies were detected—again, further demonstrating the overall safety of MicroCor®-based treatment in human subjects.

As can be seen from the data summarized in Table 4-2, relative to the Forteo® product, the MicroCor® delivery system exhibits rapid pharmacokinetic properties such as a shorter $T_{max}$, a higher $C_{max}$, and a shorter elimination half life, $T_{1/2}$, as compared to a subcutaneous injection of the agent. Absorption of hPTH (1-34) occurred more rapidly with the MicroCor® delivery system relative to the Forteo® product, as illustrated by the higher dose-normalized $C_{max}$ value and the faster $T_{max}$ values for both MicroCor® treatments. The half-life based upon administration via the MicroCor® device as also shorter than with Forteo®. Moreover, application using the MicroCor® device was more effective in achieving the desired pulsatile delivery profile of hPTH(1-34) (i.e., rapid on set and rapid offset after reaching Cmax).

The MicroCor®-based delivery results in faster elimination of drug. Based upon a plot of plasma concentration (normalized) versus time, it can be seen that the time to reach 50% of Cmax for the MicroCor®-based treatments was approximately 20 minutes for both the 32 and 64 microgram treatments (i.e., based upon the time to reach a normalized plasma concentration of 0.5). In contrast, the time to reach 50% of Cmax for the Forteo®-based treatment was approximately 1.5 hours (90 minutes), based upon time post-administration. Thus, the time to reach 50% of Cmax for the MicroCor®-based treatments was approximately 4.5 times less than that observed for subcutaneously injected PTH (Forteo®) indicating notably faster elimination of drug when administered transdermally from a microneedly array as in the MicroCor® system.

Finally, based upon a residual analysis of the PTH content of the MicroCor® delivery system following delivery of drug, it was determined that, on average, about 85% of drug was delivered from the device (i.e., 85% delivery efficiency).

It is claimed:

1. An applicator for a microprojection array, comprising:
   an energy-storing element having a first stable configuration and second stable configuration, wherein application of force to the energy-storing element causes it to transition from the first stable configuration to the second stable configuration, and wherein the force necessary for the energy storing element to transition from the first stable configuration to the second stable configuration is lower than the force necessary for the element to transition from the second stable configuration to the first stable configuration;
an actuating member that can convey external force to the energy-storing element,
a microprojection-holding member connected to the actuating member and which is acted on by the energy-storing element when it transitions from the first stable configuration to the second stable configuration,
an outer cover with an opening into which the actuating member fits slidably,
a skin-contacting member comprising a portion which can lie flat against skin, wherein the skin-contacting member fits the outer cover and contacts the energy-storing element when it is in its first configuration.

2. The applicator of claim 1, wherein the energy-storing element has an axis of symmetry and n-fold rotational symmetry for some integer n.

3. The applicator of claim 2, wherein the energy-storing element transitions from the first stable configuration to the second stable configuration upon application of force in a direction of the axis of symmetry.

4. The applicator of any claim 2, wherein the value of n is between 3 and 6.

5. The applicator of claim 2, wherein the energy-storing element is of generally frustoconical shape with slots from the top of the frustum, from the bottom of the frustum, or from both.

6. The applicator of claim 1, wherein upon application of force to the actuator member the energy-storing element transitions from its first stable configuration, wherein it is in contact with the skin-contacting member, to its second stable configuration wherein it is in contact with the outer cover.

7. The applicator of claim 1, wherein the outer cover is manufactured from a rigid material.

8. The applicator of claim 1, wherein the actuator member moves within the outer cover between a first position and a second position, wherein in its first position the actuator member extends from an upper surface of the outer cover.

9. The applicator of claim 1, wherein the actuator member moves within the outer cover between a first position and a second position, wherein in its first position the actuator member is recessed within the outer cover.

10. The applicator of claim 1, wherein a microprojection array is attached to the microprojection-holding member, the microprojection array comprises a base, and the level of the microprojection array's base is below a skin-contacting surface of the skin-contacting member following actuation of the actuating member.

11. The applicator of claim 1, wherein the energy-storing element is in mechanical coupling relationship with the microprojection-holding member when the energy-storing element is in its first stable configuration.

12. A device comprising an applicator of claim 1 and a microprojection array comprising an active agent.

13. A method of administering an active agent to a patient in need of that agent, comprising placing a device according to claim 12 on a body surface of a patient, and activating the applicator by contacting the actuator.

14. An applicator for a microprojection array, comprising:
(a) a housing having a surface with an elongated opening having platforms on opposite sides of the opening,
(b) an actuation member comprising a surface upon which a microprojection array can be attached, a generally washer-shaped surface on which an energy-storage member can be placed, and a surface capable of mating with the platforms on the opening of the housing and capable of fitting through the opening,
(c) an energy-storage member situated between the actuation member and the housing,
(d) a skin-contacting area which is generally washer-shaped connected to the housing,
wherein when the actuation member is mated with the platforms on the opening, the energy-storage member has a first force of stored energy, and
wherein when the actuation member is moved within the opening so that it no longer mates with the platforms, the energy-storage member releases its stored energy and in so doing moves the actuation member.

15. The applicator of claim 14, wherein the energy-storage member when mated with the platforms on the opening has a first force of stored energy by virtue of its being compressed.

16. An applicator according to claim 14, further comprising a safety mechanism to prevent movement of the actuation member in a direction that deploys the microprojection array.

17. The applicator of claim 16, wherein the safety mechanism comprises a protective cap over the applicator housing.

18. The applicator of claim 16, wherein the safety mechanism comprises a pin movably inserted into the actuation member on an applicator.

19. An applicator, comprising:
(a) a housing having a first member with a central opening and a second member having a skin contacting surface,
(b) an actuation member disposed in the central opening and comprising a surface upon which a microprojection array can be attached and a groove extending circumferentially,
(c) an energy-storage member having an inner edge and an outer edge, and situated within the housing initially in a first stable configuration such that the inner edge is disposed in the groove and its outer edge is in contact with the second member,
wherein application of force to the actuation member moves the energy-storage member from its first stable configuration to a second stable configuration wherein the outer edge is no longer in contact with the second member.

20. The applicator of claim 19, wherein the outer edge of the energy storage member in its second stable configuration is in contact with the first member.

21. The applicator of claim 19, wherein a microprojection array holder engages the actuation member, the engagement of the actuation member and the microprojection array holder defining the groove.

22. The applicator of claim 19, wherein the energy-storage member has an axis of symmetry and n-fold rotational symmetry for some integer n, wherein application of force in a direction of the axis of symmetry causes the energy-storing element to transition from the first stable configuration to the second stable configuration, and wherein the force necessary for the energy storing element to transition from the first stable configuration to the second stable configuration is lower than the force necessary for the element to transition from the second stable configuration to the first stable configuration.

23. The applicator of claim 22, wherein the energy-storing element is of generally frustoconical shape with slots from the top of the frustum, from the bottom of the frustum, or from both.

* * * * *